United States Patent
Gray et al.

(10) Patent No.: US 10,346,591 B2
(45) Date of Patent: Jul. 9, 2019

(54) MEDICAL DEVICE MANAGEMENT USING ASSOCIATIONS

(71) Applicant: IVENIX, INC., Amesbury, MA (US)

(72) Inventors: George W. Gray, North Andover, MA (US); William C. McQuaid, Melrose, MA (US); Jesse E. Ambrosina, Topsfield, MA (US)

(73) Assignee: Ivenix, Inc., North Andover, MA (US)

( * ) Notice: Subject to any disclaimer, the term of this patent is extended or adjusted under 35 U.S.C. 154(b) by 737 days.

(21) Appl. No.: 14/172,048

(22) Filed: Feb. 4, 2014

(65) Prior Publication Data
US 2014/0222450 A1    Aug. 7, 2014

Related U.S. Application Data

(60) Provisional application No. 61/761,119, filed on Feb. 5, 2013.

(51) Int. Cl.
*G06Q 50/00*  (2012.01)
*G06F 19/00*  (2018.01)
(Continued)

(52) U.S. Cl.
CPC ......... *G06F 19/3468* (2013.01); *A61M 5/142* (2013.01); *G16H 40/20* (2018.01);
(Continued)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS

| 5,429,602 A | 7/1995 | Hauser |
| 5,781,442 A | 7/1998 | Engleson |

(Continued)

FOREIGN PATENT DOCUMENTS

| JP | 2006155068 A | 6/2006 |
| JP | 2010266980 A | 11/2010 |

(Continued)

OTHER PUBLICATIONS

International Search Report, PCT/US2014/014467, dated May 19, 2014, pp. 4.

(Continued)

*Primary Examiner* — Tran N Nguyen
(74) *Attorney, Agent, or Firm* — Armis IP Law, LLC

(57) ABSTRACT

Via communications with an association management resource, an operator of a respective fluid delivery system can associate a medical device (fluid pump) with a particular entity such as a patient, location, one or more other medical devices, the caregiver, etc. Thereafter, the operator of the fluid delivery system is able to better manage use of the fluid delivery system based on relevant medical information, which is accessible as a result of creating the association. For example, the association management resource gathers and stores information associated with the entity prior to the operator providing the input associating the fluid delivery system with the entity. After the operator of the fluid delivery system creates the association, the medical information associated with the entity is immediately available to the fluid delivery system and/or corresponding operator of the fluid delivery system.

72 Claims, 24 Drawing Sheets

(51) Int. Cl.
*A61M 5/142* (2006.01)
*G16H 40/20* (2018.01)
*G06Q 10/00* (2012.01)

(52) U.S. Cl.
CPC ............... *A61M 2205/3561* (2013.01); *A61M 2205/6009* (2013.01)

(58) Field of Classification Search
CPC ...... G06F 19/30; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06F 19/32; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00
See application file for complete search history.

(56) References Cited

U.S. PATENT DOCUMENTS

| | | | |
|---|---|---|---|
| 6,671,563 B1 | 12/2003 | Engleson | |
| 6,731,989 B2 | 5/2004 | Engleson | |
| 6,915,170 B2 | 7/2005 | Engleson | |
| 7,096,072 B2 | 8/2006 | Engleson | |
| 7,103,419 B2 | 9/2006 | Engleson | |
| 7,107,106 B2 | 9/2006 | Engleson | |
| 7,117,041 B2 | 10/2006 | Engleson | |
| 7,171,277 B2 | 1/2007 | Engleson | |
| 7,398,183 B2 | 7/2008 | Engleson | |
| 7,454,314 B2 | 11/2008 | Engleson | |
| 7,454,341 B1 | 11/2008 | Holland et al. | |
| 7,483,756 B2 | 1/2009 | Engleson | |
| 7,895,053 B2 | 2/2011 | Engleson | |
| 8,737,195 B2 | 5/2014 | Ohashi | |
| 2002/0038392 A1* | 3/2002 | De La Huerga | A61M 5/14212 710/8 |
| 2002/0126036 A1 | 9/2002 | Flaherty | |
| 2003/0040700 A1 | 2/2003 | Hickell | |
| 2003/0060765 A1 | 3/2003 | Campbell | |
| 2003/0135388 A1 | 7/2003 | Martucci et al. | |
| 2003/0139701 A1 | 7/2003 | White | |
| 2004/0167465 A1* | 8/2004 | Mihai | A61B 5/0002 604/67 |
| 2004/0176984 A1 | 9/2004 | White | |
| 2004/0181314 A1 | 9/2004 | Zaleski | |
| 2006/0089539 A1 | 4/2006 | Miodownik | |
| 2007/0233520 A1 | 10/2007 | Wehba et al. | |
| 2009/0112630 A1 | 4/2009 | Collins, Jr. | |
| 2009/0150484 A1* | 6/2009 | Roberts | G06F 19/327 709/203 |
| 2009/0227855 A1* | 9/2009 | Hill | A61M 5/14244 600/365 |
| 2010/0287006 A1 | 11/2010 | Cannon et al. | |
| 2011/0028937 A1 | 2/2011 | Powers | |
| 2011/0202371 A1 | 8/2011 | Darguesse | |
| 2011/0238032 A1 | 9/2011 | McTaggart et al. | |
| 2011/0305376 A1* | 12/2011 | Neff | G06F 19/327 382/128 |
| 2012/0075061 A1 | 3/2012 | Barnes | |
| 2012/0135764 A1 | 5/2012 | Ohashi | |

FOREIGN PATENT DOCUMENTS

| | | |
|---|---|---|
| KR | 20090085114 A | 8/2009 |
| WO | 2006016952 A2 | 2/2006 |
| WO | 2007126948 A2 | 11/2007 |

OTHER PUBLICATIONS

Supplementary European Search Report, EP 14 74 9415, dated Feb. 1, 206, pp. 2.

* cited by examiner

MEDICAL DEVICE MANAGEMENT USING ASSOCIATIONS

RELATED APPLICATIONS

This application claims the benefit of U.S. Provisional Patent Application Ser. No. 61/761,119 entitled "Clinical Association Server," filed on Feb. 5, 2013, the entire teachings of which are incorporated herein by this reference.

This application is related to U.S. patent application Ser. No. 14/172,130 entitled "AUTOMATED PROGRAMMING OF INFUSION THERAPY," filed on the same day as the present application, the entire teachings of which are incorporated herein by this reference.

BACKGROUND

Conventional infusion pumps enable a caregiver to intravenously deliver fluid to a patient. A process of delivering fluid-based drugs requires multiple operations. For example, a physician must first generate a medication order specifying one or more fluid-based drugs for delivery to a particular patient in a hospital. Typically, a pharmacy in the hospital receives the medication order supplied by the physician. In accordance with the medication order, the pharmacy dispenses a corresponding physical order by providing the drugs to a caregiver for delivery to a respective patient.

In certain instances, the medication order includes multiple fluid-based drugs that need to be administered intravenously to the respective patient. In such an instance, and assuming that each of the fluid-based drugs must be delivered by a separate fluid delivery system (fluid pump), the caregiver overseeing the patient must locate multiple fluid delivery systems (fluid pumps) in the hospital. This itself may be a difficult task because the hospital may not keep good track of unused medical equipment.

Subsequent to locating the fluid delivery systems, the caregiver must transport the fluid delivery systems to a site where the patient resides. After the patient's bedside, in accordance with the medication order information, the caregiver operates the one or more fluid delivery systems to intravenously deliver the corresponding prescribed fluid-based drugs to the patient. Each fluid pump must be individually programmed by the caregiver to intravenously dispense the fluid to the patient.

BRIEF DESCRIPTION OF EMBODIMENTS

Conventional techniques of intravenously delivering fluid to a patient suffer from deficiencies. For example, operations of managing delivery of one or more fluids to a patient is tedious and can result in fluid delivery errors.

As a specific example, assume that a caregiver is required to administer infusion of two different types of prescribed fluids to a corresponding patient. First, as mentioned, the caregiver must retrieve two fluid delivery systems—one to deliver each of the prescribed fluid-based medicines. Thereafter, each of the fluid delivery systems has to be configured for programmed to deliver one of the multiple prescribed fluids.

In certain instances, to learn more about the different drugs that have been prescribed to the patient, and view specific details of how to administer the drugs, the caregiver has to log onto a remote computer separate from the fluid pump. The remote computer is typically at least several feet away from the actual fluid pump that is being configured to deliver the prescribed fluids to the patient. In a case of administering multiple fluids to a patient, this means that, in order to fulfill delivery of a respective medication order, the caregiver has to provide inputs to at least three different devices including a remote computer, a first fluid pump, and a second fluid pump. Thus, the caregiver must provide input to three different user interfaces, none of which may be aware of each other. The caregiver must be trained how to use each of the user interfaces—the user interface on the fluid pump and the user interface of the remote computer.

Failure to properly deliver the prescribed fluid-based drugs to a corresponding patient may be harmful, or possibly fatal. In contrast to conventional techniques, embodiments herein include unique ways of managing fluid delivery systems and related data, facilitating delivery of fluid to a recipient.

According to embodiments herein, entities in a clinical environment such as medical devices and patients can have many associations. These include, but are not limited to, associations amongst patients, locations, medical orders such as medication orders, programmed settings, care providers, medical devices, etc. Identifying associations amongst different entities allows software-based medical systems to perform more intelligently, enabling caregivers to provide a higher level of care. This could range from providing a simplified device setup process to providing smart advisories back to clinicians based on its knowledge of the collective operation of all associated devices.

One embodiment herein includes an association management resource (such as a Clinical Association Server). The association management resource allows medical devices and information systems to both register associations and utilize association mappings to identify relevant information associated with a medical task such as administering a fluid to a patient.

Embodiments herein can include a server capable of accepting, managing, and providing any number of associations between a medical device and other entities within the healthcare enterprise. Entities with which associations can be made include, but are not limited to, patients, locations, medical orders, programmed settings, care providers, other medical devices, etc.

In one non-limiting example embodiment, the association management resource exposes communication services that can be called remotely by a medical device/information system to register its own associations or to retrieve the associations of other clinical entities. In accordance with more specific embodiments, the association management resource server may optionally be configured with a set of association rules. Rules can be configured to define the impact of one association upon another, causing associations or disassociations to automatically occur as a result of the setting or resetting of others.

In accordance with yet more specific embodiments, an association management resource (such as a server resource and storage resource) receives input over a network. The input can be received from any suitable resource such as from a medical device such as a fluid delivery system that will be used to deliver fluid to a recipient. The input associates a fluid delivery system (medical device) such as a fluid pump to an entity located in a medical environment in which the fluid delivery system is operated.

Based on input received over the network, the association management resource records an association between the fluid delivery system and the entity as indicated by the received input.

The association management resource can be configured to create a different type of association depending upon the type associated with the entity. For example, if the entity is a patient, in response to receiving the input, the association management resource creates a patient-pump association between the patient and the corresponding fluid delivery system. If the entity is a location, in response to receiving input, the association management resource creates a pump-location association between the pump and the corresponding location where the pump resides. If the entity is another fluid pump, response to receiving input, the association management resource creates a pump-pump association between the first fluid pump and the second fluid pump. Accordingly, in this manner, the association management resource can create different types of associations.

Creating the association between the fluid delivery system and the entity is useful because it enables a corresponding caregiver to more efficiently operate the respective medical device such as a fluid delivery system. For example, subsequent to making an association between the entity and the fluid delivery system, the operator of the fluid delivery system can initiate a search for information associated with the entity via communications over a respective network with the association management resource.

For further sake of illustration, after creating a corresponding association, assume that the operator of the fluid delivery system transmits a request (such as a search query) for information associated with the entity over the network to the association management resource. In response to receiving the request, the association management resource searches a repository for medical information associated with the entity. Subsequent to retrieval, the association management resource initiates transmission of the medical information over the network to an operator of the fluid delivery system.

Accordingly, an operator of a respective fluid delivery system can associate a fluid delivery system (a medical device such as a fluid pump) with a particular entity such as a patient, location, one or more other medical devices, the caregiver, etc. Thereafter, the operator of the fluid delivery system is able to better manage use of the fluid delivery system based on relevant medical information, which is accessible as a result of the association.

In one embodiment, in addition to receiving input from a corresponding medical device such as a fluid pump, the association management resource gathers and stores information associated with the entity prior to the operator providing the input associating the fluid delivery system with the entity. For example, the association management resource can be configured to communicate with one or more systems in a hospital environment to retrieve information about a particular entity. In such an instance, even before a respective caregiver creates an association between the medical device and a corresponding entity, the association management resource already has information about the corresponding entity. Even before receiving input associating a particular medical device with an entity, the association management resource may have already created associations between the entity and other related entities.

As an example, the entity may be a patient in the hospital. Prior to receiving a request to associate a respective medical device (such as a pump) to the patient, the association management resource may already have collected data from one or more resources in a respective medical environment indicating that the patient is assigned to or resides in a corresponding room in a hospital. Creating a new association between the medical device and the patient indirectly associates medical device with a corresponding room in which the patient resides.

In one embodiment, after an operator of the fluid delivery system creates an association between the fluid delivery system and the entity, the medical information associated with the entity is immediately available to the fluid delivery system and/or corresponding operator of the fluid delivery system.

As another example, prior to receiving the input indicating to create a new association between a medical device (such as a fluid pump) and a corresponding entity such as a patient, association information produced by the association management resource the association management resource can indicate that the patient has been prescribed one or more fluid drugs. After creating the new association between the medical device and the patient, an operator of the medical device is able to access the association management resource to identify information related to the patient such as the prescribed one or more fluid drugs.

Note that the input from an operator of the fluid delivery system (medical device) can be received from any suitable resource. For example, in accordance with one embodiment, the fluid delivery system can include a display screen configured to display a graphical user interface. Additionally, via software instructions executing in the fluid delivery system, the fluid delivery system can be configured to communicate with the association management resource over a corresponding network connection. The operator of the fluid delivery system provides input to the graphical user interface of the medical device to associate the medical device with a particular entity. The medical device forwards the association request over the respective network connection to the association management resource.

As mentioned, subsequent to creating a corresponding association between the fluid delivery system and a respective entity, the operator of the fluid delivery system can use the graphical user interface to perform a search query to obtain medical information associated with the entity over the network connection. As previously discussed, in response to receiving a search query from the fluid delivery system, the association management resource retrieves and transmits appropriate medical information to the fluid delivery system.

In accordance with yet further embodiments, note that the operator of the fluid delivery system does not necessarily need to use a graphical user interface physically located on the fluid delivery system in order to perform tasks such as associate the fluid delivery system to a corresponding patient, retrieve medical information, etc. For example, an operator of the fluid delivery system (such as a caregiver that uses the fluid delivery system to deliver a corresponding fluid-based drug to a patient) may be assigned a management device to facilitate giving care to one or more patients. The management device can be a handheld management device that is disparately located with respect to the fluid delivery system operated to deliver fluid to a corresponding patient.

In certain embodiments, the operator of the fluid delivery system can initiate creation of an association between a medical device and another entity via input to a corresponding display screen on the handheld management device. Thus, an association between a fluid delivery system and a respective entity can be achieved in a number of different ways depending on the embodiment.

These and other more specific embodiments are disclosed in more detail below.

Note that any of the resources as discussed herein can include one or more computerized devices, fluid delivery systems, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware or shortcode in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: receive input over a network, the input associating a fluid delivery system to an entity located in a medical environment in which the fluid delivery system is operated; record an association between the fluid delivery system and the entity as indicated by the received input; search a repository for medical information associated with the entity; and initiate transmission of the medical information over the network to an operator of the fluid delivery system.

The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for managing and facilitating use of medical devices. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

Figure 1:
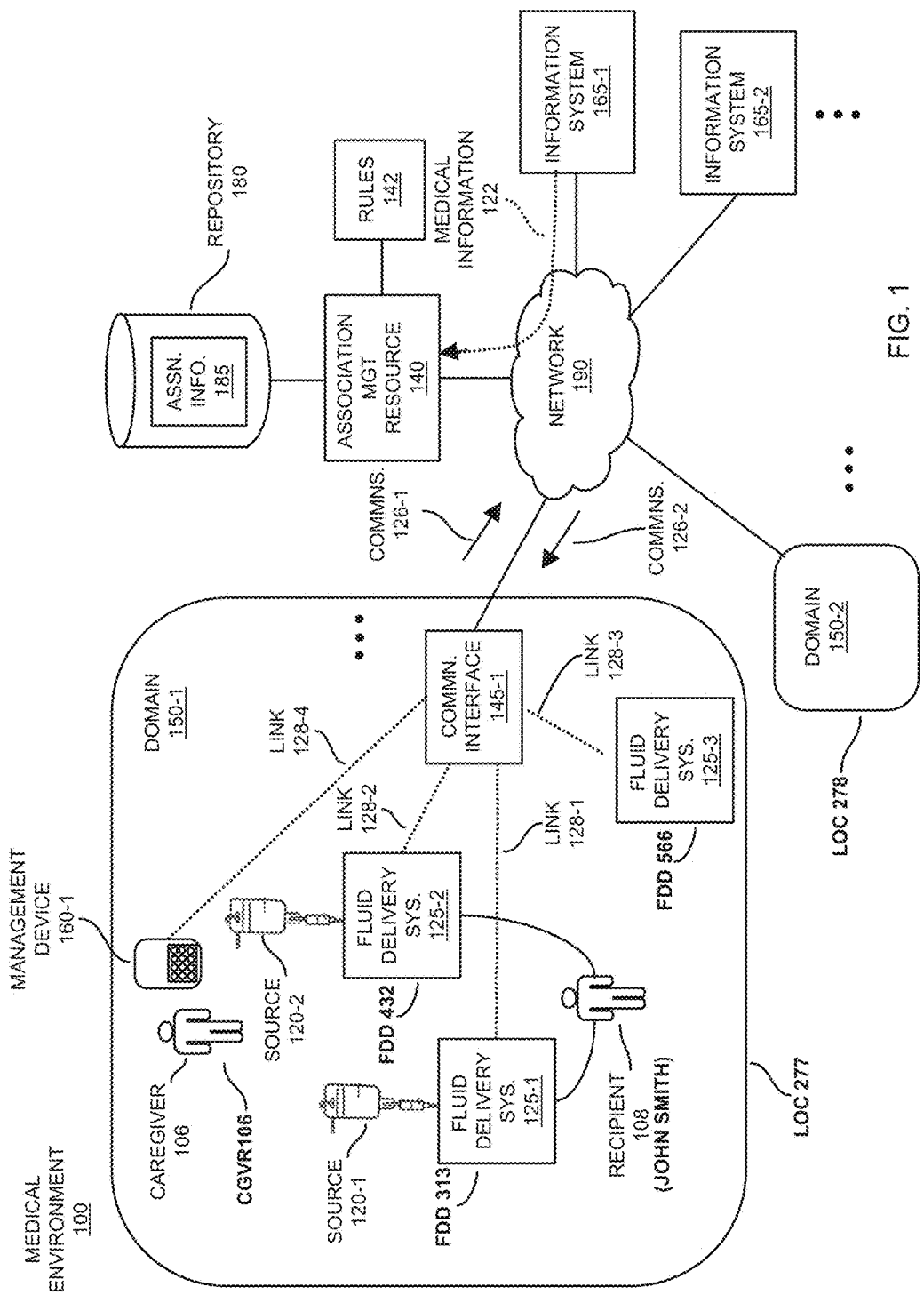
FIG. 1 is an example diagram illustrating association management in a medical environment according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

Now, more specifically, FIG. 1 is an example diagram illustrating association management and fluid delivery management in a medical environment according to embodiments herein.

As shown, medical environment 100 includes network 190 (which may include a packet-switched network, the Internet, WiFi™ network, etc.), association management resource 140, information system 165, domain 150-1, domain 150-2, etc.

Each of the domains 150 (e.g., domain 150-1, domain 150-2, etc.) in medical environment 100 can represent a location in medical environment 100 in which fluid is delivered to a corresponding recipient. A fluid delivery domain can represent a hospital room, a person's home, etc.

In this non-limiting example embodiment, assume that caregiver 106 configures fluid delivery system 125-1 (such as first pump) to deliver fluid from source 120-1 to recipient 108. Assume math the caregiver 106 configures fluid delivery system 125-2 (such as a second pump) to deliver fluid from source 120-2 to recipient 108. Recipient 108 in this example is patient John Smith.

Note that domain 150-1 further includes communication interface 145-1. In one embodiment, each of the medical devices in domain 150-1 has the ability to communicate with communication interface 145-1. In this example embodiment, each of the fluid delivery systems 125 is communicatively coupled to communication interface 145-1 via a respective communication link (such as a wired communication link, wireless communication link etc.).

In this non-limiting example embodiment, communication link 128-1 supports communications between fluid delivery system 125-1 and communication interface 145-1; communication link 128-2 supports communications between fluid delivery system 125-2 and communication interface 145-1; communication link 128-3 supports communications between fluid delivery system 125-3 and communication interface 145-1; communication link 128-4 supports communications between management device 160-1 and communication interface 145-1; and so on.

Each of the communication links 128 can be a hardwired or wireless link.

Any suitable protocol can be employed to communicate RF and/or hardwired communications between each of the devices and communication interface 145-1 over a respective communication link. In one embodiment, each of the communication links 128 supports communications in accordance with the WiFi™ protocol.

As further shown, communication interface 145-1 supports communications 126-1 through network 190 to any of one or more remotely located resources such as association management resource 140, information system 165, etc.

In a reverse direction, communication interface 145-1 receives communications 126-2 from the one or more remotely located resources in network 190. Communication interface 145-1 forwards the received communications 126-2 to the appropriate resource (such as a medical device) in domain 150-1.

Accordingly, each of the one or more resources such as fluid delivery system 125-1, fluid delivery system 125-2, fluid delivery system 125-3 (such as third fluid pump), management device 160-1, etc., is able to communicate with any of one or more resources located in medical environment 100 through communication interface 145-1 and over network 190.

In one embodiment, each of the devices or systems in medical environment 100 is assigned a corresponding unique network address. Via client-server type communications, each of the devices or systems in the medical environment is able to communicate with a respective remotely located resource. For example, using a network address of the association management resource 140 in respective generated data packets, any of the medical devices located in medical environment 100 are able to transmit the generated data packets to association management resource 140. In a reverse direction, the association management resource 140 can include a network address of a corresponding target medical device in generated data packets to forward such communications to the target medical device.

In one non-limiting example embodiment, the resources in medical environment 100 (such as each of the fluid delivery systems 125, management device 160-1, association management resource 140, etc.) communicate amongst each other via a HyperText Transfer Protocol (HTTP) type protocol. By way of non-limiting example, the resources can communicate via using secure HTTP (i.e., HTTPS), ensuring that communications and the connections between the association management resource 140 and the fluid delivery systems are secure and that messages are fully encrypted.

As shown, and as previously discussed, embodiments herein include an association management resource 140. In accordance with one embodiment, and along the other functions, the association management resource 140 collects information (such as medical information 122) associated with different resources in the medical environment 100 from one or more resources.

As its name suggests, the association management resource 140 manages associations. By way of non-limiting example, based on received data, the association management resource 140 produces and manages association information 185 stored in repository 180.

As its name suggests, the association information 185 managed by association management resource 140 keeps track of associations amongst the different entities in medical environment 100.

In accordance with yet further embodiments, each of the entities in the medical environment 100 is assigned a corresponding unique value.

For sake of illustration, assume that caregiver 106 is assigned to the unique value CGVR 106; fluid delivery system 125-1 is assigned the unique value FDD 313; fluid delivery system 125-2 is assigned a unique value FDD 432; fluid delivery system 125-3 is assigned the unique value FDD 566; domain 150-1 in medical environment 100 is assigned the unique value LOC 277; domain 150-2 in medical environment 100 is assigned a unique value LOC 278; and so on.

Each of the domains 150 in medical environment 100 can include similar resources as domain 150-1.

As further discussed below, association management resource 140 produces and manages association information 185 to keep track of associations between the different resources or entities in medical environment 100.

Note that associations can change over time. For example, the association management resource 140 can receive communications from any resource in medical environment 100 (such as information system 165, domain 150-1, domain 150-2, etc.) indicating to create one or more new associations.

Additionally, in addition to receiving communications to create new associations, the association management resource 140 can receive communications indicating to terminate one or more associations. Thus, the state of association information 185 stored in repository 180 changes over time.

By further way of a non-limiting example, the association management resource 140 can be configured to implement a set of association rules 142 to manage respective associations between entities in medical environment 100. In one embodiment, these rules 142 help automate the association and disassociation of entities. For example, a rule may state that when two medical devices are associated, they also share the same patient and location associations. Thus, the rules 142 can specify how to create associations.

Association rules 142 may be defined for the entire institution (medical environment 100) or may be domain or device type specific. This enable rules for an intensive care unit to differ from rules used in an operating room. Use of different rules would also allow, for example, association rules between two infusion pumps to differ from those between an infusion pump and a patient monitor.

Figure 2:
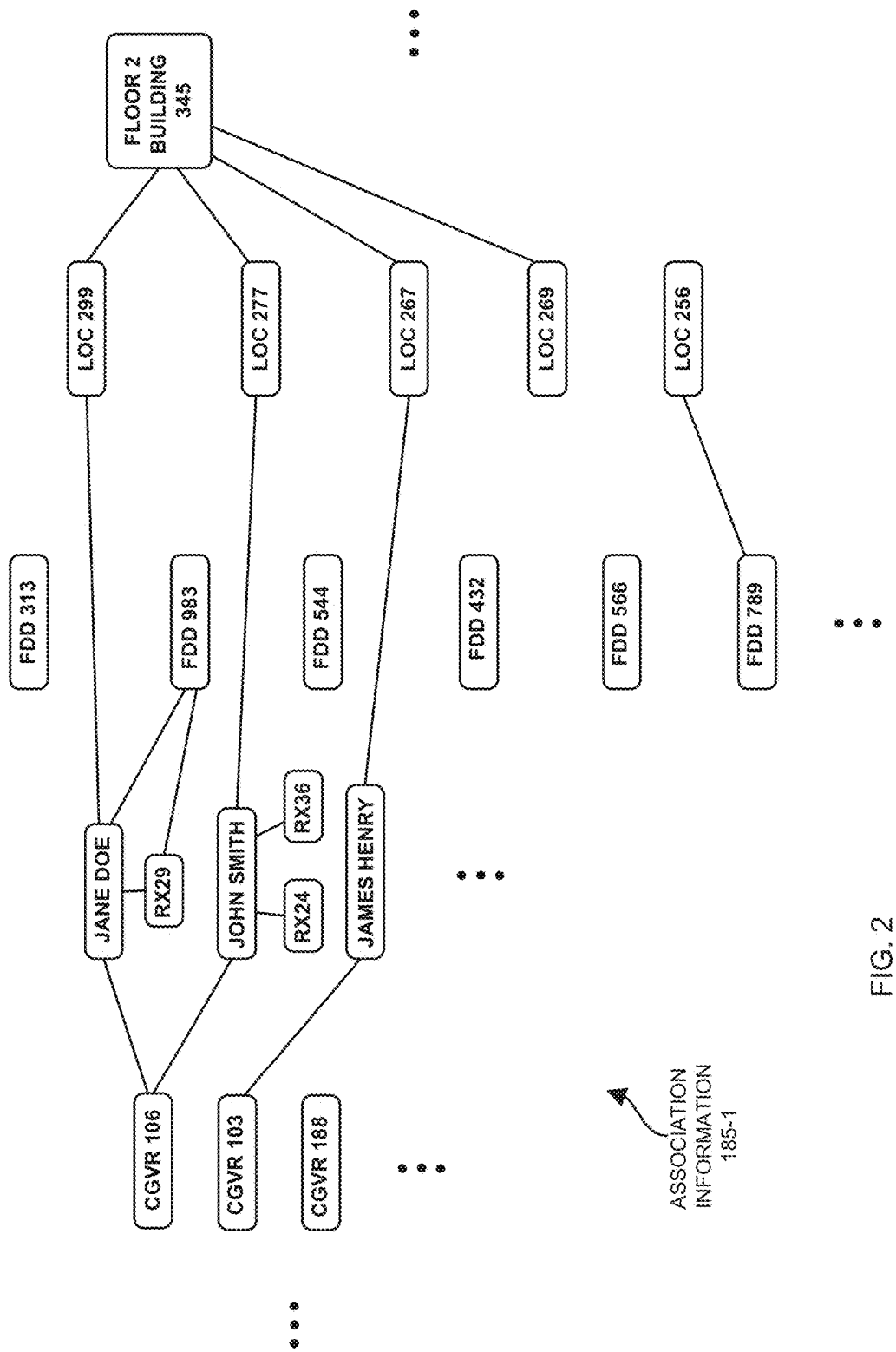
FIG. 2 is an example diagram illustrating management of associations amongst different entities in a medical environment according to embodiments herein.

FIG. 2 is an example diagram illustrating association information according to embodiments herein. As shown in this example, the association information 185-1 indicates associations (as represented by a line) between different types of entities in the medical environment 100. Each node in FIG. 2 represents a corresponding entity or resource in or associated with medical environment 100.

Further note that management of the associations amongst the different entities can be achieved in any number of ways. For example, the association management resource 140 can employ any suitable resource such as pointers, tables, mappings, etc., can be used to indicate the associations amongst the different entities.

Associations can be created continuously over time. For example, in one embodiment, association management resource 140 is configured to constantly search network 194 for information related to entities located in medical environment 100. In the example embodiment shown, the association management resource 140 receives medical information 122-1 from information system 165-1; the association management resource receives medical information 122-2 from information system 165-2; and so on.

Medical information 122 can be any suitable type of information. For example, the medical information can be patient information, billing information, physician information, medication order information (such as one or more prescription drug orders), caregiver information, location information, etc.

Recall that each of the entities in medical environment 100 is assigned a unique value. Based on information received from one or more resources in medical environment 100, the association management resource 140 creates association information 185-1 to indicate current associations amongst different entities or resources located in medical environment 100.

Note that medical environment 100 is not limited to a corresponding location such as a hospital. Medical environment 100 can include any resource, entity, etc., that is related to patient care.

In this example, via respective caregiver-patient association lines in FIG. 2, association information 185-1 indicates that: caregiver CGVR 106 (caregiver 106) has been assigned to care for patients Jane Doe and John Smith; caregiver CGVR 188 is not assigned to care for anyone; and so on. Thus, associations in the association information 185 can indicate assignments.

Further in this example, via respective medicine-patient association lines, association information 185-1 indicates that: fluid-based drug RX29 has been prescribed to Jane Doe; fluid-based drugs RX24 and RX36 have been prescribed to John Smith; and so on.

As previously discussed, the association management resource 140 can be configured to receive association information from any suitable resource. In one embodiment, the association management resource 140 receives medical information 122-1 from information system 165-1 indicating that a physician has prescribed fluid-based drugs RX24 and RX36 to John Smith. Based on receipt of this medical information (medication order information), the association management resource 140 creates the association lines between medication order drugs RX24 and RX36 and John Smith.

Yet further in this example, via the respective patient-location association lines, association information 185-1 indicates that: patient Jane Doe resides in a respective domain LOC 299 (such as a first hospital room); patient John Smith resides in domain LOC 277 (such as a second hospital room); patient James Henry resides in domain LOC 267 (such as a third hospital room); and so on.

James Henry has been assigned to caregiver CGVR 103.

Still further in this example embodiment, via respective domain-building association lines, association information 185-1 indicates that: the domain assigned LOC 299 is located on the second floor of building 345; the domain assigned LOC 277 is located on the second floor of building 345; the domain assigned LOC 267 is located on the second floor of building 345; the domain assigned LOC 269 is located on the second floor of building 345; the domain assigned LOC 269 is located on the second floor of building 345; and so on.

As may be expected, certain associations in the association information 185 are static. That is, location LOC 299 (such as a first room in a hospital) will always reside in the second floor of building 345; location LOC 277 (such as a second room in a hospital) will always reside in the second floor building 345; location LOC 267 (such as a third room in a hospital) will always reside in the second floor building 345; and so on.

Other associations are temporary. For example, caregiver CGVR106 may be temporarily assigned to care for John Smith and Jane Doe during a first shift. When switching over to a second shift, the caregiver CGVR188 may be assigned to care for Jane Doe and John Smith instead of caregiver CGVR106. In such an instance, in response to detecting this change, the association management resource 140 would create a respective association between caregiver CGVR188 and each patient Jane Doe and John Smith. Additionally, the association management resource 140 may terminate an association between caregiver CGVR106 and Jane Doe and John Smith.

Yet further in this example embodiment, the respective pump-patient association lines, association information 185-1 indicates that: the fluid delivery system assigned the unique value FDD 983 has been assigned for use by Jane Doe.

In response to detecting that a caregiver such as caregiver CGVR106 currently dispenses medication order RX 29 prescribed to Jane Doe using the fluid pump FDD 983, the association management resource 140 produces an association line between the medication order RX29 and the fluid delivery system FDD 983. The association line between the prescribed drug RX29 and fluid delivery system FDD 983 indicates that the fluid delivery system FDD 983 is being used or has been assigned to deliver the prescribed drug RX 29 to patient Jane Doe.

Using the association information 185-1, it is possible to identify the status of fluid deliveries as well as assignments of different medical devices to different patients. In other words, the associations enable one to identify different types of information associated with medical care. For example, via the associations in association information 185-1 presented in FIG. 2, the corresponding user is able to identify that caregiver CGVR106 has been assigned to care for patient Jane Doe and that caregiver CGVR106 has configured pump FDD 983 to deliver medication order RX29 to Jane Doe.

As previously discussed, the association management resource 140 creates associations between the different entities as specified by association information 185 based on input. For example, the association management resource 140 can be a computer server running on a local area network. The association management resource 140 is capable of communicating with medical devices/information systems connected either directly or wirelessly to that network 190.

By further way of a non-limiting example, the server exposes one or more communication services. These services utilize one or more communication mechanisms. For example, one service may be capable of communicating using RESTful web services while another, performing the same function, may support SOAP based web services. Each communication service is capable supporting one or more functions, including but not limited to, registering, modifying and/or unregistering clinical associations and returning association details to those that request that information.

As previously discussed, the association information 185 can be configured to maintain a history of associations made over time such that it is possible to view prior existing associations between entities at a given snapshot in time. In one embodiment, the association management resource 140 produces the association information 185 to keep track of the history of the associations made over time. The retrieval of the history information from association information 185 stored in repository 180, a respective user is able to keep track the occurrence of different types of events.

All maintained associations can be made available to medical devices or any component capable of interacting through the server communication services.

As shown in the association information 185-1 in FIG. 2, note that there is currently no association between John Smith and any of the fluid delivery systems located in domain 150-1. In this example embodiment, the association management resource 140 has not receiving information indicating that fluid delivery system 125-1, fluid delivery system 125-2, and fluid delivery system 125-3 reside in domain 150-1 (LOC 277).

In one embodiment, each of the fluid delivery systems can be configured to occasionally or periodically broadcast information indicating the presence at a particular location. In such an instance, a nearby communication interface at the location (such as communication interface 145-1) may receive the communication and forward the location information to association management resource 140. Accordingly, based on the received location information in corresponding entity, the association management resource 140 can create an association between each of the fluid delivery systems and a corresponding location in which the fluid delivery system resides. Alternatively, note that a caregiver may be required to operate a corresponding fluid delivery system to create a new association between the fluid delivery system and a location in which the fluid delivery system resides. Thus, association of a respective medical device (such as a fluid delivery system) can be automated or required that a caregiver manually associated a respective fluid delivery system with a location.

Referring again to FIG. 1, in this example embodiment, assume that there currently is no association between any of the fluid pumps (fluid delivery systems 125) in domain 150-1 and a corresponding recipient 108 such as patient John Smith.

Assume in this example that caregiver 106 (assigned the unique value CGVR106) receives notification that the medication orders RX24 and RX25 need to be administered to recipient 108. The notification can be received on any suitable medical device. In one embodiment, the caregiver 106 receives the notification on medical device 160-1 assigned to and operated by the caregiver 106.

To associate respective one or more fluid delivery systems to recipient to administer the medication orders, the caregiver 106 initiates communications with association management resource 140. For example, the caregiver 106 inputs association information to association management resource 140 to indicate the fluid delivery system 125-1 and fluid delivery system 125-2 are being assigned to John Smith.

Supplying the association information to association management resource 140 can be achieved in any suitable manner.

In one embodiment, the caregiver 106 provides the input (association information) associating the fluid delivery system 125-1 to John Smith through a graphical user interface of fluid delivery system 125-1.

Figure 3:
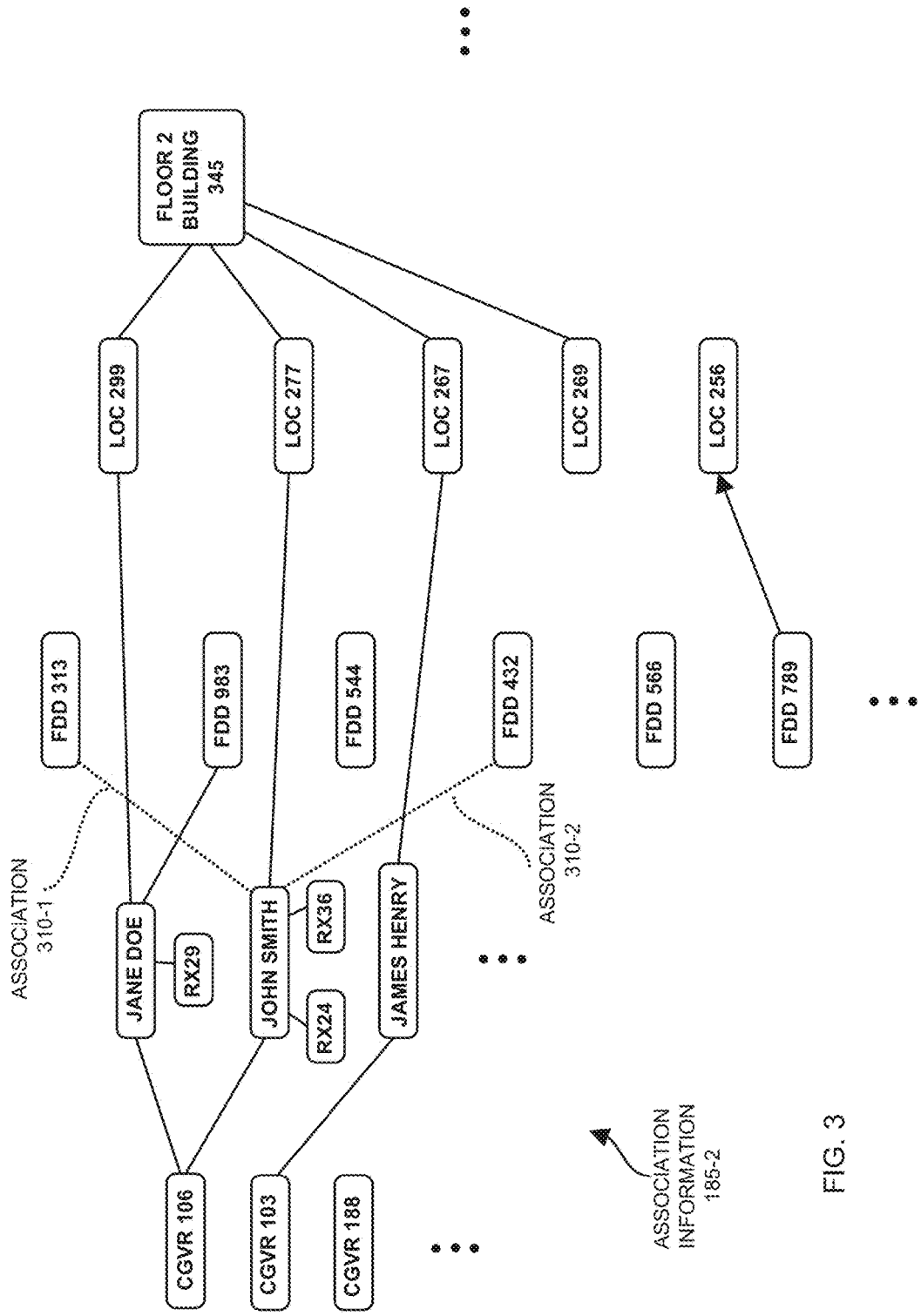
FIG. 3 is an example diagram illustrating association of a medical device to an entity in a medical environment according to embodiments herein.

In response to receiving the input, the fluid delivery system 125-1 communicates the pump-patient association information over communication link 128-1 to communication interface 145-1. Communication interface 145-1 further communicates the input over network 190 to association management resource 140. The association management resource 140 receives the input generated by the caregiver 106 and updates the corresponding association information 185-2 as shown in FIG. 3 to indicate that the fluid delivery system 125-1 (FDD 313) has been assigned for use by recipient 108 (John Smith). In this example embodiment, as shown in FIG. 3, in response to receiving the input notification from the caregiver 106 (CGVR 106) that the fluid delivery system 125-1 (FDD 313) has been assigned for use by recipient 108 (John Smith), the association management resource 140 creates a new patient-pump association 310-1 between recipient 108 (John Smith) and fluid delivery system 125-1 (FDD 313).

For further sake of illustration, assume that the caregiver 106 operates in graphical user interface of fluid delivery system 125-2. In one embodiment, the caregiver 106 (CGVR 106) provides the input (association information) associating the fluid delivery system 125-2 to John Smith through fluid delivery system 125-2 (FDD 432).

In response to receiving this further input from the caregiver 106, the fluid delivery system 125-2 (FDD 432) communicates this new pump-patient association information over communication link 128-2 to communication interface 145-1. Communication interface 145-1 further communicates the input over network 190 to association management resource 140. The association management resource 140 receives the input generated by the caregiver 106 and updates the corresponding association information 185-2 as shown in FIG. 3. In this example embodiment, as shown in FIG. 3, in response to receiving the input notification from the caregiver 106 that the fluid delivery system 125-2 (FDD 432) has been assigned for use by recipient 108 (John Smith), the association management resource 140 creates a new patient-pump association 310-2 between recipient 108 (John Smith) and fluid delivery system 125-2 (FDD 313).

Note that the notification generated by caregiver 106 indicating assignment of the fluid delivery system 125-1 (FDD 313) for use by recipient 108 (John Smith) can be submitted from any suitable resource. For example, as discussed above, the respective caregiver 106 can operate a respective graphical user interface of a corresponding fluid delivery system to communicate the association information to association management resource 140. However, note that in accordance with further embodiments, the caregiver 106 can operate a graphical user interface of management device 160-1 to input the association information to association management resource 140. In this latter instance, the management device 160-1 transmits the association information received from the caregiver 106 over communication link 128-4 to communication interface 145-1. Communication interface 145-1 communicates the association information through network 190 to association management resource 140. In a manner as previously discussed, the association management resource 140 utilizes the received information to create the association between the patient John Smith and the one or more fluid delivery systems.

Accordingly, via generation of association information from any suitable resource, embodiments herein can include creating an association between a medical device and a corresponding entity such as a patient in the medical environment 100.

Creating the associations 310-1 and 310-2 between the fluid delivery systems and the patient is useful because it enables a corresponding caregiver 106 to more efficiently operate the fluid delivery systems assigned to recipient 108 (John Smith). For example, subsequent to making association between the recipient 108 and the fluid delivery systems, using respective graphical user interfaces of the fluid delivery systems 125, the operator (caregiver 106) of the fluid delivery systems can initiate a search for information associated with the recipient 108 (John Smith) to obtain useful information.

For further sake of illustration, assume that the caregiver 106 provides input to a corresponding graphical user interface of the fluid delivery system 125-1 to transmit a request for information associated with an entity such as recipient 108 from fluid delivery system 125-1 over the network 190 to the association management resource 140. In response to receiving the request, the association management resource 140 searches a repository for medical information associated with the entity to which the fluid delivery system has been assigned. In this example flow delivery system 125-1 has been assigned to recipient 108 (John Smith).

The caregiver 106 may be interested and retrieving information regarding prescribed drugs prescribed to recipient 108 (John Smith). In such an instance, via communications through fluid delivery system 125-1 or management device 160-1, the query from the caregiver 106 to association management resource 140 would indicate that the caregiver 106 would like information about one or more different drugs prescribed to the corresponding recipient 108 (John Smith).

In response to receiving the query, the association management resource 140 accesses association information 185 shown in FIG. 3 to identify that John Smith has been assigned use of fluid delivery system 125-1 (FDD 313) and fluid delivery system 125-2 (FDD 432) by caregiver 106. Additionally, via the association information 185, the association management resource 140 identifies that medication orders RX24 and RX36 both have been assigned to recipient 108 (John Smith). In one embodiment, the association management resource 140 initiates retrieval of medical information (such as medication order information) associated with medication orders RX24 and RX36 from repository 180 or other suitable resource.

In one embodiment, medication order information associated with a respective medication order can be stored as one or more retrievable objects for retrieval and viewing by the respective caregiver. The medication order information in a respective retrievable object can indicate parameters such as a type of fluid were type of drug to be delivered to the corresponding patient, a rate at which the fluid will be delivered to the corresponding patient, a time when the fluid should be dispensed to the corresponding patient, etc.

Subsequent to retrieval of the medical information or object, the association management resource 140 initiates transmission of the medical information over the network 190 to fluid delivery system 125-1. In accordance with associations identified by association management resource 140, fluid delivery system 125-1 initiates display of the medical information associated with medication orders RX 24 and/or RX 36 on a respective graphical user interface displayed on a display screen of fluid delivery system 125-1 for viewing by caregiver 106.

Accordingly, association of the fluid delivery system to a corresponding patient enables the caregiver to easily retrieve information (such as medication order information) associated with the corresponding patient.

Note that association of the fluid delivery systems to a corresponding patient is shown by way of non-limiting example. As previously discussed, embodiments herein can include use of a medical device to create any suitable types of associations. For example, further embodiments herein can include associating a fluid delivery system (fluid pump)

with any suitable entity such as a location, one or more other medical devices, another fluid pump, a caregiver, etc. As discussed above, creation of an association makes it possible for a respective caregiver to retrieve and view related medical information associated with the entity to which the medical device has been assigned.

Figure 4:
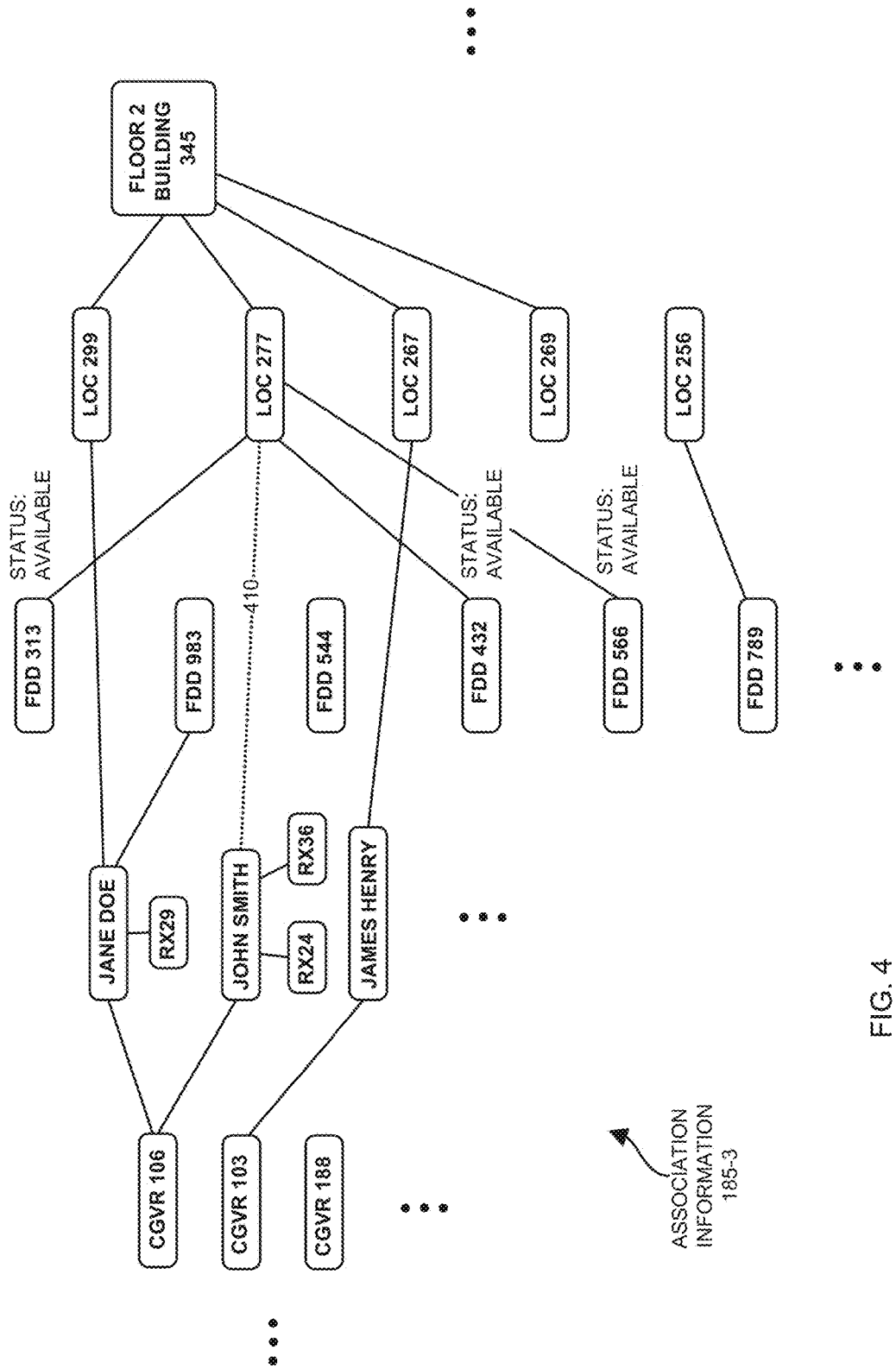
FIG. 4 is an example diagram illustrating management of associations amongst different entities in a medical environment according to embodiments herein.

FIG. 4 is an example diagram illustrating creation of associations amongst different entities in a medical environment according to embodiments herein.

In this example embodiment, assume that the recipient 108 (John Smith) has recently been transported into domain 150-1. Accordingly, association information 185-3 does not yet indicate an association between John Smith and corresponding domain 150-1 (LOC 277).

Assume that the association management resource 140 receives notification that John Smith has been moved into domain 150-1. In response to receiving notification that the recipient 108 (John Smith) has been moved into domain 150-1, the association management resource 140 updates the association information 185-3 in FIG. 4 to include association 410 to indicate that the patient John Smith now resides in domain 150-1 (LOC 277).

The notification that the recipient 108 has been moved into domain 150-1 can be received from any suitable resource. For example, in one embodiment the caregiver 106 can operate management device 160-1 to notify association management resource 140 that the recipient 108 now resides in domain 150-1.

In accordance with an alternative embodiment, information system 165 can be configured to keep track of the location of each of the patients in the medical environment 100. In such an embodiment, the information system 165 can be configured to forward the location information (medical information) associated with the recipient 108 to the association management resource 140.

Further in this example embodiment, assume that the association management resource 140 receives input from each of the fluid delivery systems 125 indicating their location. Thus, in this example, the association information 185-3 managed by association management resource 140 indicates that: fluid delivery system 125-1 (FDD 313) is available and associated with domain 150-1 (LOC 277); fluid delivery system 125-2 (FDD 432) is available and associated with domain 150-1 (LOC 277); fluid delivery system 125-3 (FDD 566) is available and associated with domain 150-1 (LOC 277), and so on. Because the fluid delivery systems 125-1, 125-2, and 125-3 are not currently assigned for use by a particular patient, the association information 185-3 indicates that such fluid delivery systems are available.

Thus, in addition to managing associations amongst each of the different entities in medical environment 100, the association management resource 140 can be configured to maintain status information associated with each of the entities as well.

Figure 5:
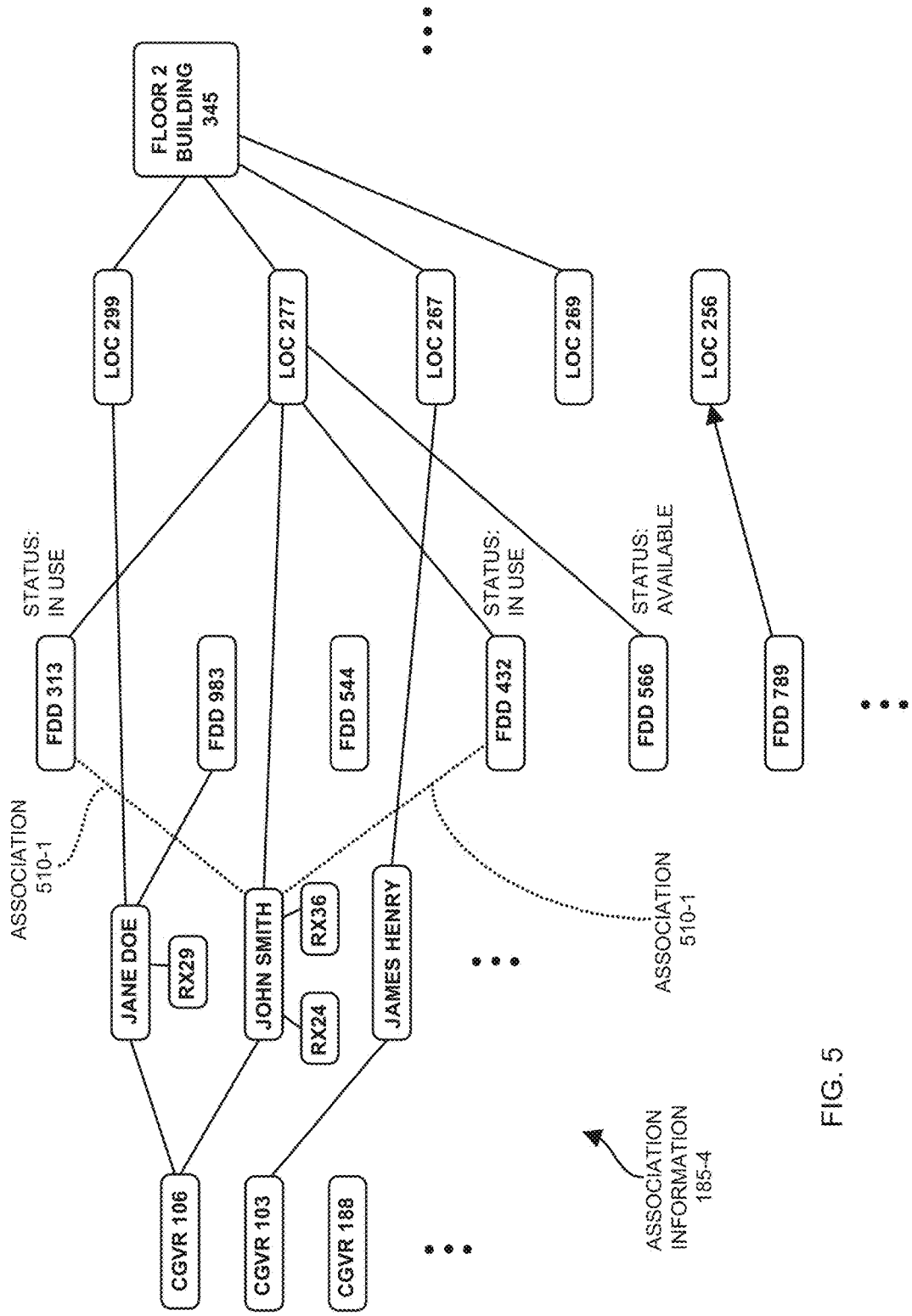
FIG. 5 is an example diagram illustrating association of a medical device to an entity according to embodiments herein.

Assume further in this example embodiment that the caregiver 106 operates fluid delivery system 125-1 (FDD 313) to transmit association information to association management resource 140. As previously discussed, the fluid delivery system 125-1 transmits the association information (associating the fluid delivery system 125-1 to recipient 108) over communication link 128-1 to communication interface 145-1. Communication interface 145-1 further communicates the association information generated by caregiver 106 (or other suitable resource) to association management resource 140. In response to receiving the association information, the association management resource 140 updates the association information 185-4 as shown in FIG. 5 to indicate the new association 510-1 between the fluid delivery system 125-1 (FDD 313) to recipient 108 (John Smith). That is, the new association 510-1 indicates that the fluid delivery system 125-1 (FDD 313) has been assigned for use by recipient 108 (John Smith).

Assume further in this example embodiment that the caregiver 106 operates fluid delivery system 125-2 (FDD 432) to transmit association information to association management resource 140. As previously discussed, the fluid delivery system 125-2 transmits the association information (associating the fluid delivery system 125-2 to recipient 108) over communication link 128-2 to communication interface 145-1. Communication interface 145-1 further communicates the association information generated by caregiver 106 to association management resource 140. In response to receiving the association information, the association management resource 140 updates the association information 185-4 in FIG. 5 to indicate the new association 510-2 between the fluid delivery system 125-1 (FDD 313) and recipient 108 (John Smith).

In a manner as previously discussed, association of the fluid delivery systems with one or more entities in the medical environment 100 makes it easy for the caregiver 106 or other user to retrieve information associated with the interconnected entities.

Each node in the association information 185 can include status information associated with the respective entity. For example, as previously discussed, association information 185 includes node representing John Smith. The node representing John Smith can include an object such as one or more files or documents associated with John Smith. The information in the object associated with John Smith can indicate information such as an age of the patient, gender of the patient, medical history, nature of an injury, allergies, etc. In other words, the object assigned to John Smith can include any useful information that would be helpful for providing care to John Smith while he resides in medical environment 100.

In a similar manner, the node associated with a respective caregiver can indicate useful information such as a name of the caregiver, the current location of the caregiver, the title of the caregiver such as whether the caregiver is a nurse or doctor, contact information of the caregiver, etc.

As previously discussed, because the fluid delivery systems have been associated with the different entities in the medical environment 100, the fluid delivery systems can be used to retrieve useful information. For example, a user in domain 150-1 can provide commands to a corresponding graphical user interface of fluid delivery system 125-1 to retrieve and display useful information on a respective display screen of the fluid delivery system 125-1.

Assume that the user of the fluid delivery system 125-1 generates a command to retrieve personal information associated with the recipient 108 (John Smith) to which the fluid delivery system 125-1 has been assigned. In such an instance, the user initiates transmission of the command to the association management resource 140 to retrieve the personal information about recipient 108 (John Smith). In response to receiving the command, the association management resource 140 retrieves the object assigned to the node John Smith in the association information 185 and forwards it to the fluid delivery system 125-1 for display on a corresponding display screen.

Accordingly, the associations make it possible to retrieve useful information associated with the recipient 108.

Figure 6:
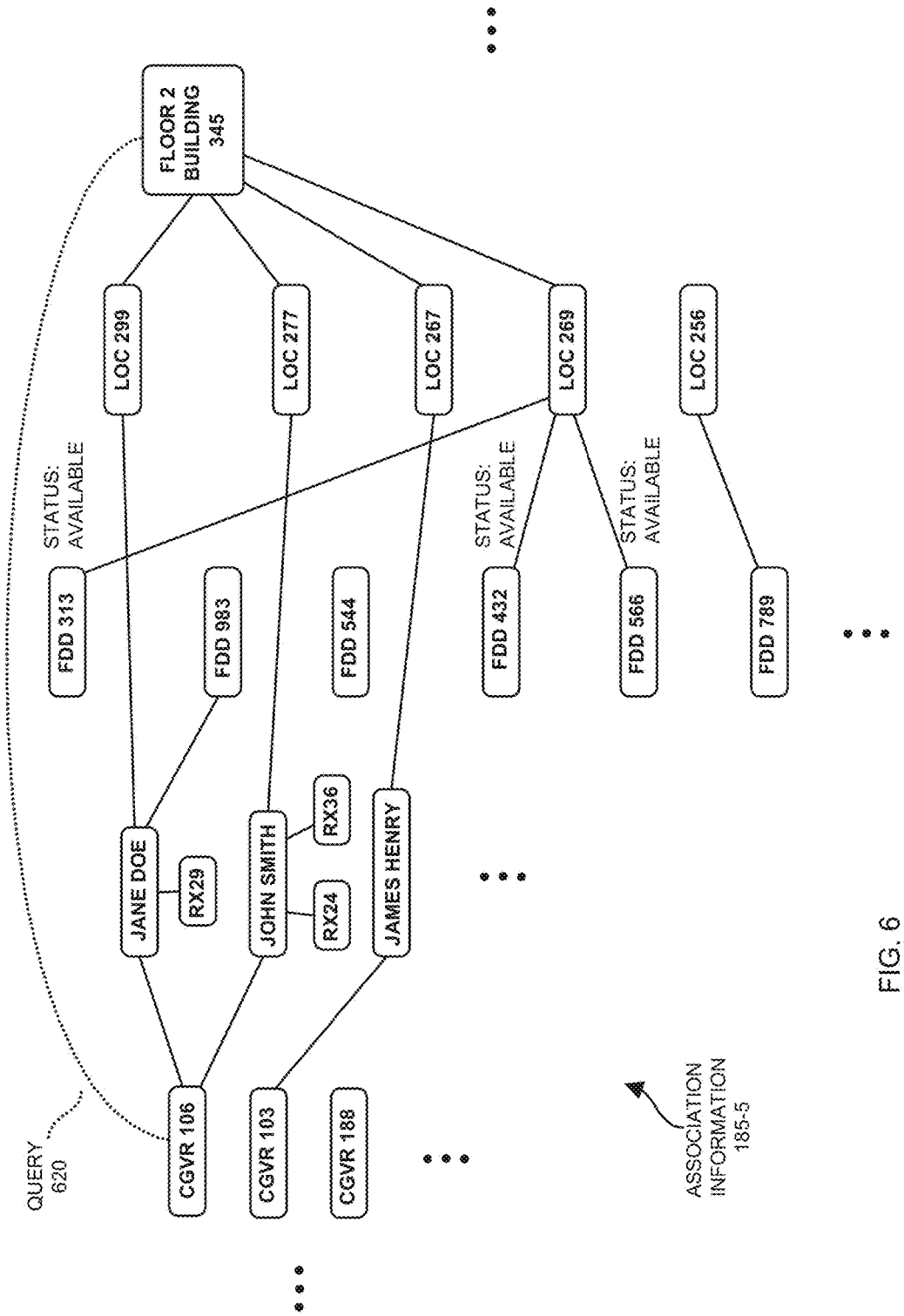
FIG. 6 is an example diagram illustrating management of associations amongst different entities in a medical environment according to embodiments herein.

FIG. 6 is an example diagram illustrating creation of associations between different entities in a medical environment according to embodiments herein.

Assume in this example embodiment that the patient John Smith has been moved into domain 150-1 (LOC 277) and that the caregiver 106 receives notification that John Smith requires administration of multiple medication orders including RX24 and RX25. Assume further that the fluid delivery systems 125-1, 125-2, and 125-3, are initially located in a room (LOC 269) other than domain 150-1 (LOC 277) where they are needed. The caregiver 106 realizes that she will need to retrieve fluid delivery systems in order to administer the medication orders assigned to John Smith.

In one embodiment, to search for availability of fluid delivery systems, the caregiver 106 operates management device 160-1 and generates query 620 to learn of the availability of fluid delivery systems on floor two of building 345. The caregiver 106 forwards the query to association management resource 140.

In response to receiving the query 620, the association management resource 140 analyzes association information 185-5 and identifies that fluid delivery system 125-1 (FDD 313), fluid delivery system 125-2 (FDD 432), and fluid delivery system 125-3 (FDD 566) are all located in a nearby room (LOC 269) with respect to domain 150-1 (LOC 277).

The association management resource 140 transmits this information for display on management device 160-1 for viewing by caregiver 106. Based on such information, indicating that available fluid delivery systems are located at location LOC 269, the caregiver 106 walks to the hospital room (LOC 269) to move fluid delivery system 125-1 (FDD 313) and fluid delivery system 125-2 (FDD 432) into domain 150-1.

Figure 7:
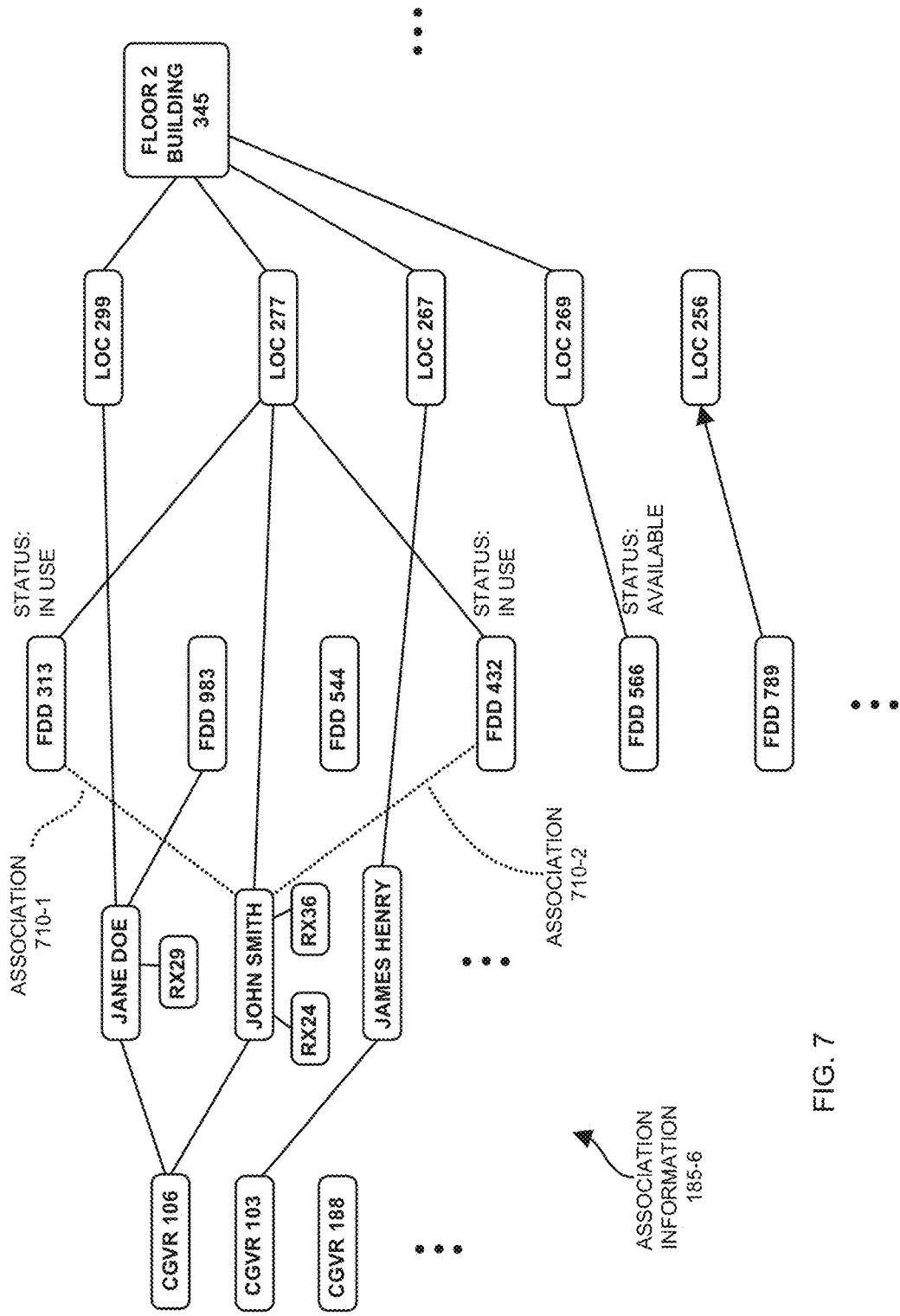
FIG. 7 is an example diagram illustrating association of an entity to a medical device according to embodiments herein.

As shown in FIG. 7, in response to detecting movement of the fluid delivery systems 125-1 and fluid delivery system 125-2 into domain 150-1, the association management resource 140 can receive updates indicating that the fluid delivery systems have been moved into domain 150-1 (LOC 277). In response to detecting this condition (that fluid delivery system 125-1 and fluid delivery system 125-2 have been moved into domain 150-1), as shown in FIG. 7, the association management resource 140 updates association information 185-6, creating an association between the fluid delivery system 125-1 (FDD 313) and domain 150-1 (LOC 277); the association management resource 140 creates an association between the fluid delivery system 125- to (FDD 432) and domain 150-1 (LOC 277).

Even though the fluid delivery system 125-1 and 125-2 have been moved into domain 150-1, the association management resource 140 can be configured to maintain the status of these fluid delivery systems as being available because they have not yet been assigned to a corresponding patient.

Further in this example embodiment, assume that the caregiver 106 produces and transmits association information to association management resource 140 indicating that fluid delivery system 125-1 and fluid delivery system 125-2 have been assigned for use by recipient 108 (John Smith).

In such an instance, and in response to receiving the notification of new associations to be created, the association management resource 140 creates new association 710-1 to indicate that the fluid delivery system 125-1 (FDD 313) has been assigned for use by recipient 108 (John Smith); the association management resource 140 creates new association 710-2 to indicate that the fluid delivery system 125-2 (FDD 432) has been assigned for use by recipient 108 (John Smith).

In a manner as previously discussed, subsequent to creating the associations, the respective fluid delivery system and or other management device can be used to retrieve useful information associated with the interrelated entities.

Figure 8:
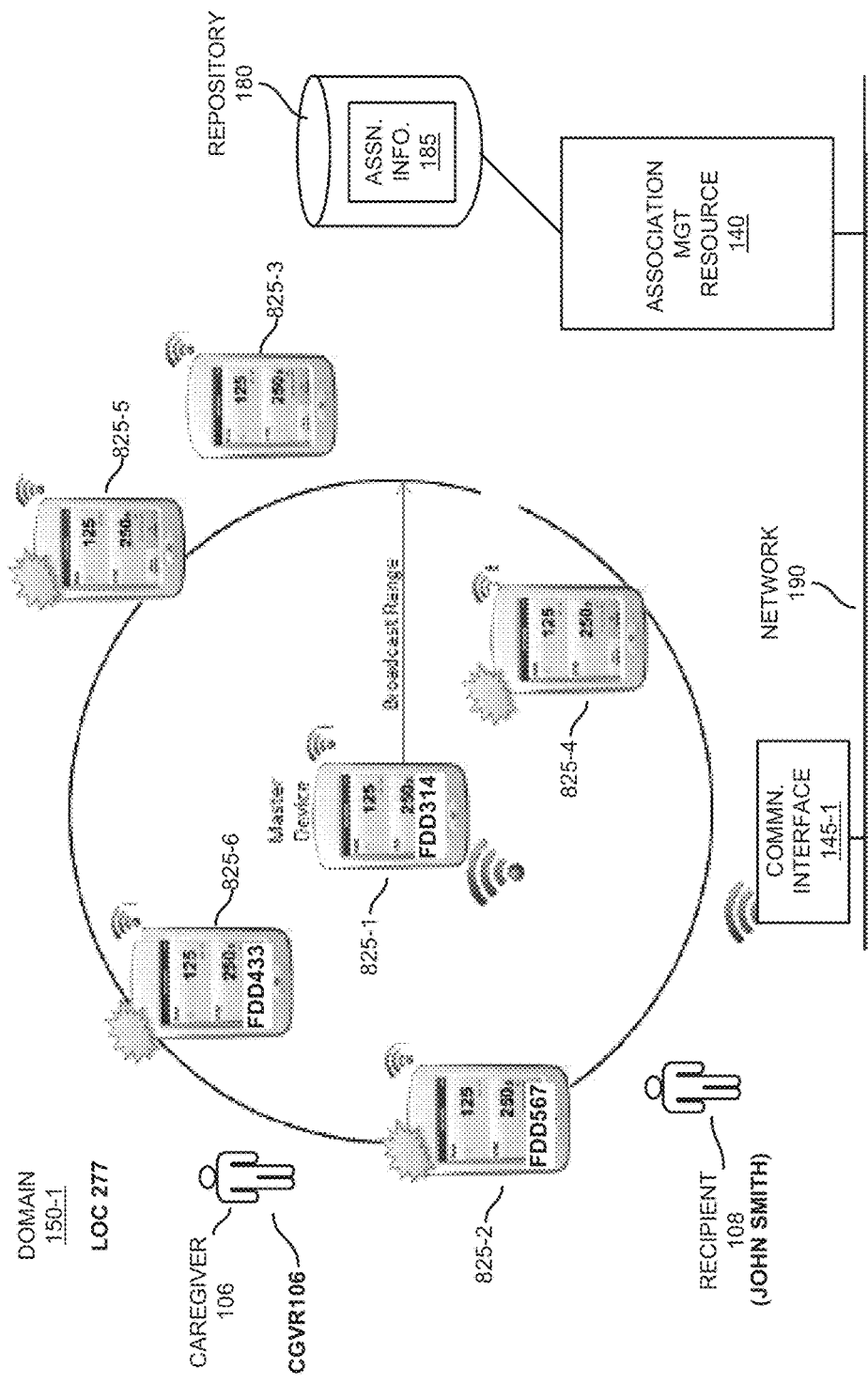
FIG. 8 is an example diagram illustrating proximity association according to embodiments herein.

FIG. 8 is an example diagram illustrating proximity association according to embodiments herein.

Conventional medical devices typically operate independently and autonomously from one another even when those devices are connected to the same patient. As part of the setup of each device, a clinician or caregiver identifies both the location of the device and the patient association. In the event that multiple medical devices exist at a bedside, the same, time consuming association process must be performed with each device in order to associate the medical device with the other devices or patient. In other words, conventional methods require that the caregiver operate each of the devices independently to associate that device with a particular patient or other entity.

According to embodiments herein, given the existence of the association management resource 140, devices (such as fluid delivery systems 125, medical device 160-1, etc.) may associate with a device designated as a master device, form a group and inherit the location and patient associations of that master device. This significantly reduces the overall setup time of each subsequent device and reduces the probability of error during that process. As further discussed below, creation of a group of medical devices can be achieved in any suitable manner.

Proximity association as described herein enables medical devices to form associations with one another through a few simple user interactions. For example, using a wireless communication, such as Bluetooth, Near Field Communication (RFC), RFID or similar near distance RF technology, etc., a medical device such as a fluid delivery system (master device) can be configured to transmit an invitation to nearby devices to join it in a group. Any available devices within range of this master device respond to the transmission, giving users and devices the option to join the group. For those that accept the invitation to join the group, an association is created between the two devices and the associated patient and location of the master device are synchronized with those joining the group.

In one embodiment, although user interaction is required to initiate the formation of a group from one device and confirm membership in a group on another device, interactions can be straightforward and minimal. As part of the formation of the group, a personal area or piconet network is formed between the devices and the patient and location associations maintained by the master device is synchronized with each new group member.

In accordance with more particular embodiments herein as shown in medical environment 800 of FIG. 8, proximity association can include a system made up of one or more medical devices 825 and association management resource 140 (such as a clinical association server).

In this non-limiting example embodiment, each of the medical devices 825 can be configured to include a wireless transceiver (transmitter and receiver). For example, medical device 825-1 includes a transceiver to communicate with any other medical devices in medical environment 800; medical device 825-2 includes a transceiver to communicate with any other medical devices in medical environment 800; medical device 825-3 includes a transceiver to communicate with any other medical devices in medical environment 800; medical device 825-4 includes a transceiver to communicate with any other medical devices in medical environment 800;

medical device 825-5 includes a transceiver to communicate with any other medical devices in medical environment 800; and so on.

From any medical device, a user may initiate the formation of a new group. The device from which an operator such as a caregiver initiates formation of the new group is referred to herein as the master device. In this example embodiment, assume that the medical device 825-1 is the master device. To initiate a group, the master device transmits a broadcast message to other medical devices located in the medical environment 800. In one embodiment, the broadcast message is transmitted as an RF signal within domain 150-1.

In accordance with further embodiments, as a possible alternative to communicating the RF broadcast signal directly to the other medical devices, note that the medical device 825-1 can be configured to communicate with the association management resource 140 to identify nearby medical devices. In response to receiving a message from the medical device 825-1 that the operator would like to create a new grouping, the association management resource 140 can be configured to communicate over network 190 and communication interface 145-1 to medical devices 825-2, 825-3, 825-4, etc., in domain 150-1 to indicate that the caregiver 106 might to create the new grouping.

Accordingly, the other non-master medical devices in domain 150-1 can receive the invitation to join the new grouping in a number of different ways. For example, the medical devices in domain 150-1 can receive a communication directly from the master medical device 825-1 or receive notification from the association management resource 140.

Any medical device that receives the invitation and is available can join the group. For example, when a device receives the invitation message generated by master medical device 825-1, the medical device receiving the invitation message prompts the user (via a respective notification on a display screen of the receiving device) to acknowledge or reject the group invitation on its local user interface for viewing by a caregiver. Thus, in this example embodiment, the display screen of medical device 825-2 displays a message that a nearby master medical device 825-1 generated a corresponding invitation to join a group; the display screen of medical device 825-3 displays a message that a nearby master medical device 825-1 generated a corresponding invitation to join a group; the display screen of medical device 825-4 displays a message that a nearby master medical device 825-1 generated a corresponding invitation to join a group; and so on.

The visual prompt displayed on each of the medical devices receiving the broadcast message from medical device 825-1 indicates that medical device 825-1 has initiated formation of a medical device grouping. The visual prompt can indicate patient and location information associated with a particular patient for which the association is being created. Display of the visual prompt on each of the medical devices receiving the broadcast message gives the caregiver the option to join the group.

More specifically, assume that the caregiver would like medical device 825-1, medical device 825-6, and medical device 825-2, to be part of the grouping. Because the medical device 825-1 initiated the broadcast message inviting other medical devices to possibly join the group, medical device 825-1 is already part of the new grouping.

To add medical device 825-6 to the grouping, the operator (such as caregiver 106) in domain 150-1 provides input to the graphical user interface displayed on display screen of medical device 825-6 indicating that medical device 825-6 has joined the new grouping.

To add medical device 825-2 to the grouping, the operator provides input to the graphical user interface displayed on display screen of medical device 825-2 indicating that medical device 825-2 has joined the new grouping.

In one embodiment, in response to receiving input that the operator would like a respective medical device included in the new grouping, the respective medical device transmits a message to the other medical devices or association management resource 140 indicating that it has joined the new grouping. Each of the medical devices can be configured to display a listing of the current members of the new grouping.

In accordance with further embodiments, the user reviews the members of the group from any device in the group and can optionally remove itself or other members from the group.

When a device joins a group, it connects to a local network such as piconet network of the master device. It then inherits the patient and location associated with the master medical device 825-1. Thus, if the master medical device 825-1 has been associated with recipient 108 (John Smith), then each of the medical devices 825-6 and 825-2 become associated with the recipient 108 (John Smith).

By way of non-limiting example, once complete, the devices can be configured to notify association management resource 140 of its association with the group and its associated patient and location information. In a manner as previously discussed, the association management resource 140 creates and stores the associations amongst the medical devices and the new grouping. The association information is stored centrally and available to other devices in the system via the association management resource 140.

Figure 9:
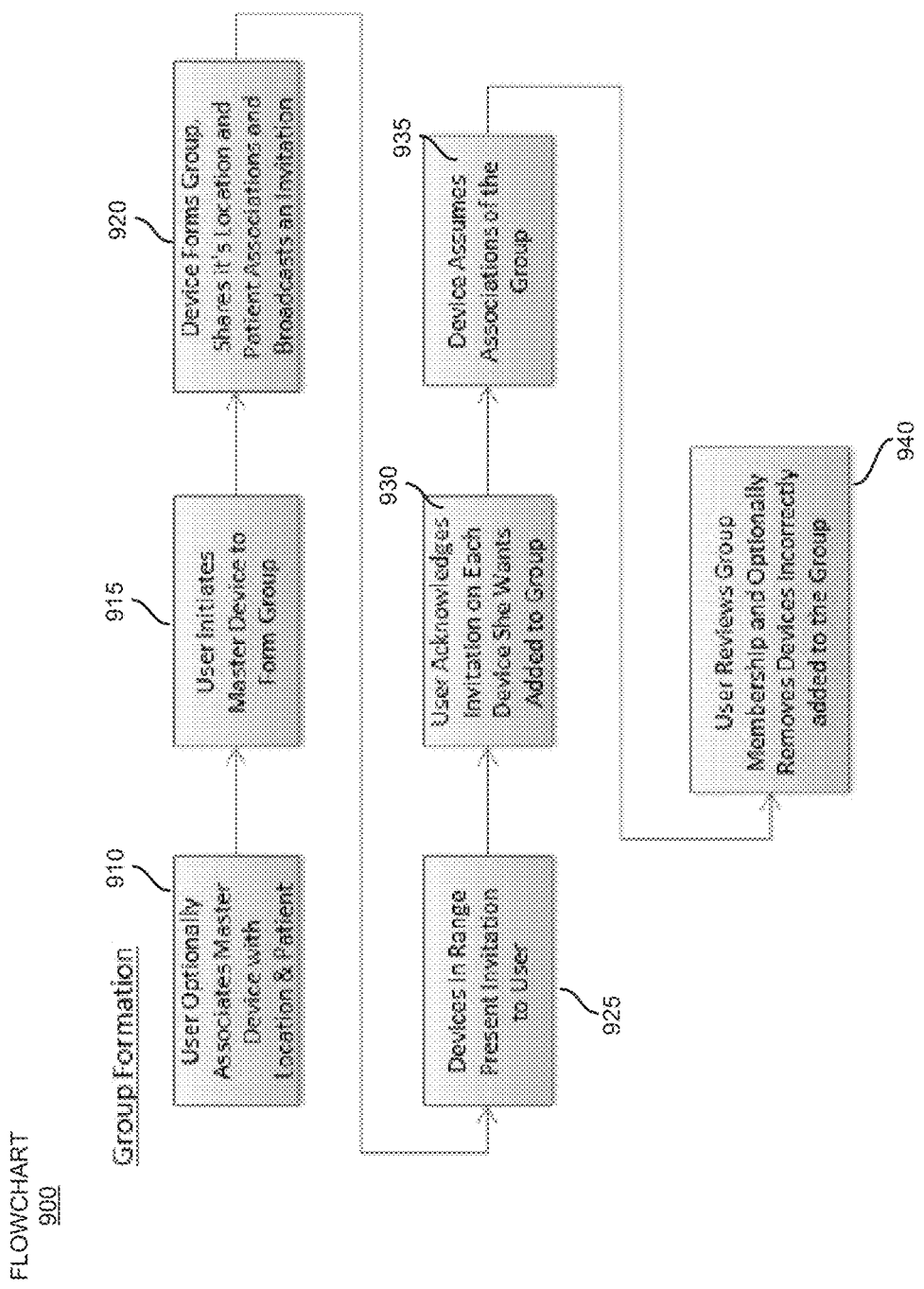
FIG. 9 is an example diagram of a method illustrating formation of a medical device grouping and creation of associations amongst one or more medical devices according to embodiments herein.

FIG. 9 is an example diagram of a flowchart illustrating formation of a group and creation of associations amongst one or more medical devices according to embodiments herein.

In processing block 910 a flowchart 900, the caregiver 106 optionally associates the master medical device 825-1 with corresponding location and/or patient information.

In processing block 915, the caregiver 106 operates the master medical device 825-1 to form a new grouping.

In processing block 920, the master medical device 825-1 forms a new grouping, shares his location and patient association information and broadcast a corresponding invitation to other potential members. In response to receiving a command to form a grouping, the medical device 825-1 (such as a first fluid delivery system) or association management resource 140 initiates communication with a set of one or more medical devices located in a vicinity of the medical device 825-1 (first fluid delivery system).

In processing block 925, each of the medical devices that receive the invitation initiates display of a query on a corresponding display screen of a medical device asking the user whether or not the device should be included in the new grouping. In one embodiment, each of the medical devices activates a prompt indicating that the respective medical device displaying the prompt can be programmed to join a group including the fluid delivery system.

In processing block 930, the caregiver provides input to each of the medical devices that are to be included in the new grouping.

In processing block 935, the medical devices that accept the invitation to join the group assume the associations of the group members.

In processing block 940, the caregiver 106 optionally reviews the new grouping and removes any medical devices that were incorrectly added to the new grouping.

Note again that creation of the grouping amongst multiple medical devices can be performed in any suitable way. For example, in accordance with another embodiment, and with reference again to FIG. 1, the caregiver 106 can operate fluid delivery system 125-1 in order to learn of other fluid delivery systems located in a corresponding vicinity. In this example embodiment assume that in response to transmitting a query to association management resource 140, association management resource 140 transmits a response to fluid delivery system 125-1 indicating that fluid delivery system 125-2 and fluid delivery system 125-3 are also located within domain 150-1 based on the association information 185. Accordingly, the association management resource 140 can provide notification to an operator (caregiver 106) of the fluid delivery system 125-1 that fluid delivery system 125-2 and fluid delivery system 125-3 are available in a vicinity of the fluid delivery system 125-1.

Via input into a graphical user interface of the fluid delivery system 125-1, the caregiver 106 can select delivery system 125-2 and fluid delivery system 125-3 in order to form a respective grouping. Assume that the fluid delivery system 125-1 communicates a request to form this new grouping to association management resource 140. Assume further in this example that the request indicates that the fluid delivery system 125-1 would like to form a group including fluid delivery system 125-1 and fluid delivery system 125-2.

In response to receiving the request to form the new grouping, the association management resource 140 associates the fluid delivery system 125-1 and fluid delivery system 125-2. The association management resource 140 records the association between the fluid delivery system 125-1 and the fluid delivery system 125-2.

Figure 10:
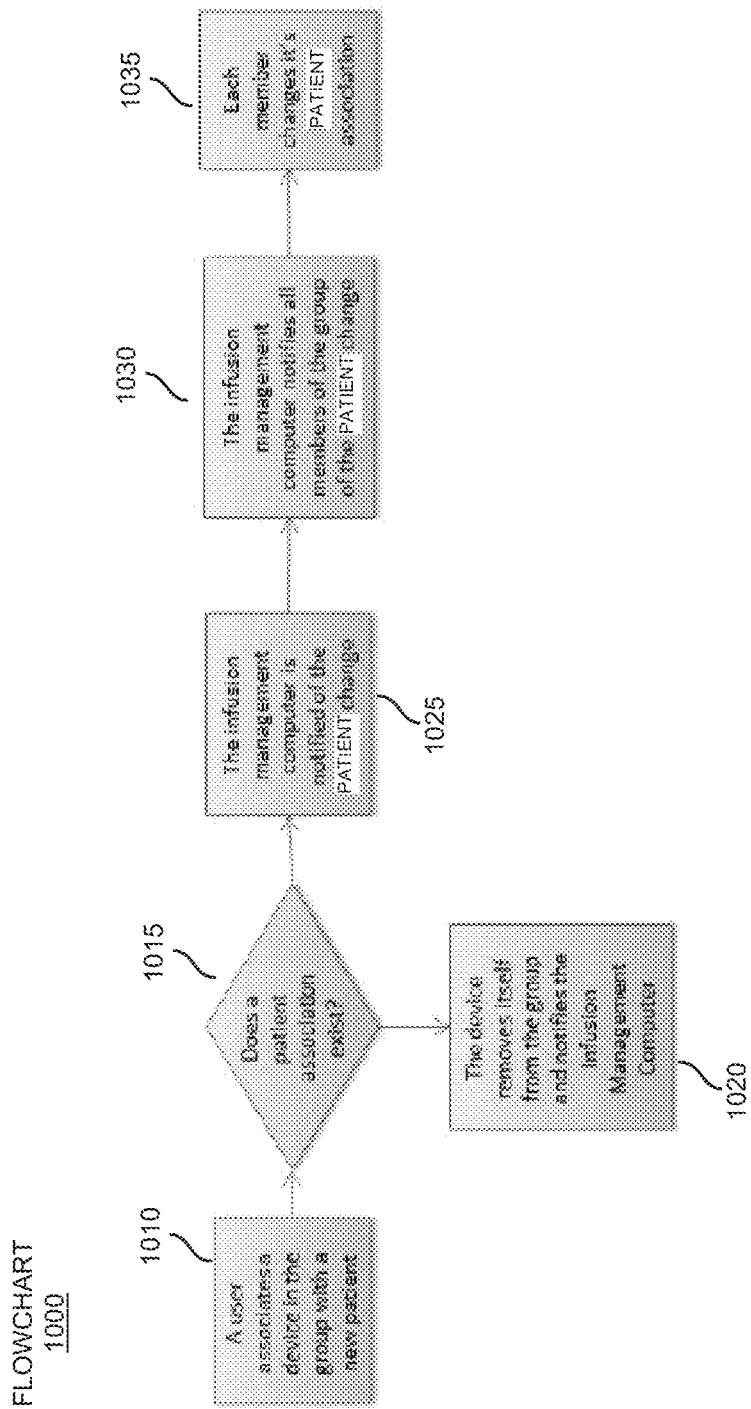
FIG. 10 is an example diagram of a method illustrating association of a group of medical devices to a corresponding patient according to embodiments herein.

FIG. 10 is an example diagram illustrating a patient association according to embodiments herein.

When a new grouping of medical devices has not yet been associated with a patient, embodiments herein include creating an association between a selected patient and each medical device in the new grouping at a time when the selected patient is assigned for the first time to any of the medical devices in the newly formed grouping.

In accordance with one embodiment, at the time of associating the new grouping of medical devices with a patient, a notification will be sent via wide area wireless technology, such as WiFi™, to the other devices in the group, indicating that the association now exists. This gives the user the option of accepting it or opting out of the group.

Once a group has an associated patient, that patient association with the respective medical device cannot be changed. Changing the patient association with a respective medical device in the group will cause that device to be disassociated from the group. This avoids the possibility that a respective medical device (or new grouping of medical devices) will be inadvertently assigned to multiple patients.

As shown flowchart 1000, in processing block 1010, the user associates a device in the group with a new patient.

In processing block 1015, a respective medical device determines whether a patient association already exists with a particular medical device. If so, processing continues at processing block 1020. If not processing continues at processing block 1025.

In processing block 1020, in response to detecting that the corresponding medical device is already associated with a patient, the medical device removes itself from the grouping and produces a corresponding notification.

In processing block 1025, in response to detecting that the corresponding medical device is currently not associated with a particular patient, and that the user associates the corresponding medical device with a new patient, the corresponding medical device associates itself with the news patient.

In processing block 1030, the corresponding medical device notifies other medical devices in the group of the association with the new patient.

In processing block 1035, each of the medical devices in the grouping that receives the notification of the association between the corresponding medical device and new patient updates their association to the new patient as well. Thus, when a single medical device in the grouping updates its association with a particular new patient, each of the other medical devices in the grouping updates their association with the new patient as well.

Figure 11:
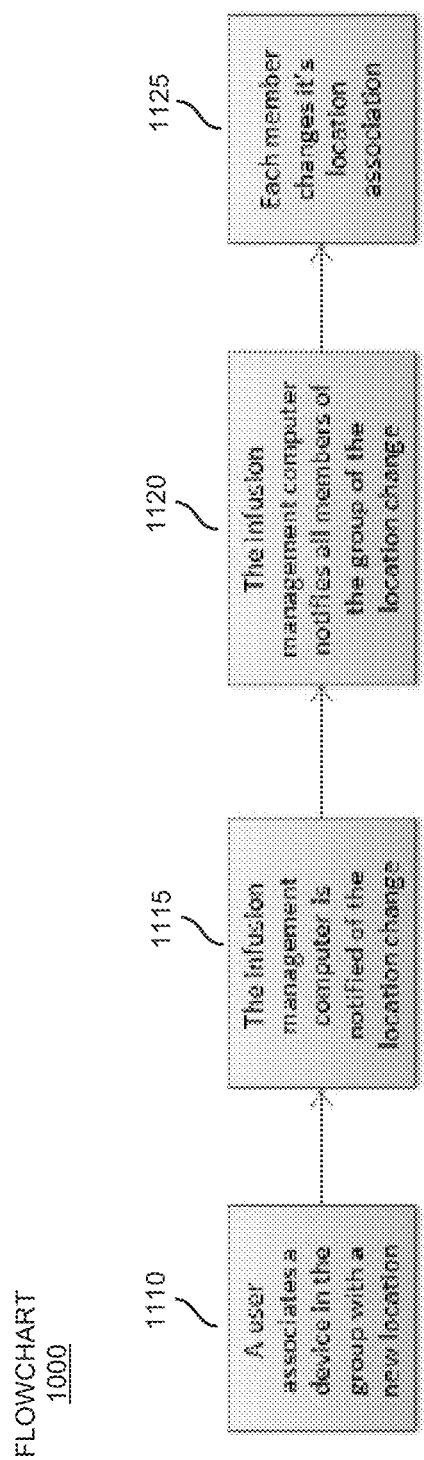
FIG. 11 is an example diagram of a method illustrating association of a group of medical devices to a corresponding location according to embodiments herein.

FIG. 11 is an example diagram illustrating location association according to embodiments herein.

Initially, the newly established grouping of medical devices may not be associated with a particular location. When a group of medical devices has no location association, this association will be set the first time any device in that group forms a respective association with location.

In one embodiment, at the time of associating one of the medical devices and the grouping to a location, a notification is sent by the association management resource 140 via a wide area wireless technology, such as Wi-Fi™, to each medical device in the group. This causes each of the medical devices to update location association. Thus, when one of the medical devices in the grouping becomes associated with a particular location, all of the medical devices in the group become associated with the particular location.

Note that a group's location association can be changed at any time. Doing so will result in a notification being sent by the association management resource 140 via a wide area wireless technology, such as Wi-Fi™, to each device in the group and cause each device to update its location.

As further shown in flowchart 1100 of FIG. 11, in processing block 1110, the caregiver 106 or other suitable resource associates a given medical device in the new grouping with a new location.

In processing block 1115, the caregiver 106 operates the given medical device to associate the given medical device with the new location.

In processing block 1120, the given medical device notifies all members of the newly formed group of the location change.

In processing block 1125, in response to receiving the notification from the given medical device, each medical device in the grouping changes its location association to the location as indicated by the association management resource 140.

Thus, association of one of the medical devices in the grouping to a corresponding location causes each of the other members in the grouping to be associated with the corresponding location.

As previously discussed, one embodiment herein includes transmitting appropriate information to the association management resource 140 to indicate the creation of the new associations.

In one embodiment, when the caregiver 106 exits the group formation utility on the master device, the device ceases to transmit and all devices disconnect. However, their association with the group remains intact.

As previously discussed, each of the medical devices can be configured to provide the ability to disassociate itself with the respective group it has joined. A device will also automatically be removed from a group if a user attempts to form a new group from that device or associates the device with a different patient.

Proximity Association Extensions:

1. Embodiments herein can include creating state or programmed settings information for each of the medical devices in a respective grouping. In one embodiment, a respective medical device produces state information associated with the respective medical device. The respective medical device forwards the state information to association management resource 140 for storage in repository 180. Any of the members in the grouping can communicate with the association management resource 140 to learn of the settings associated with the other medical devices. Thus, each of the medical devices in the grouping can be made aware of settings associated with other medical devices in the grouping.

2. In accordance with another embodiment, a grouping may include a first fluid delivery system and a second fluid delivery system assigned for use by the same patient. As previously discussed, the association management resource 140 can be configured to store settings information associated with each of the fluid delivery systems. The second fluid delivery system can be configured to communicate with the association management resource 140 to learn that the first fluid delivery system has been configured to deliver the same medicine as the second fluid delivery system. In such an instance, assuming that the infusion of the same drug from multiple different fluid delivery systems is a mistake, the second fluid delivery system (and/or first fluid delivery system) can be configured to generate a warning (such as an audible or visual warning) of the condition. The caregiver then takes corrective action.

3. In a similar vein, the second fluid delivery system can be configured to issue a warning notification to the caregiver 106 if the drug the second fluid delivery system is about to deliver is incompatible with a drug being delivered from the first fluid delivery system.

In a similar vein, the second fluid delivery system can be configured to issue a warning notification to the caregive 106 if the drug the second fluid delivery system is about to deliver results in a dangerous interaction with the drug being delivered from the first fluid.

4. Using information retrieved in #1 and knowledge of a scheduled order or order set, an unused but associated infusion device may prompt the user to allow it to auto-program itself to support a next scheduled treatment.

5. Using information retrieved in #1, an infusion device may issue a warning if the total fluid volume being infused into a respective patient is unsafe.

6. Any device in the group may disassociate with the group without impacting the remaining associations in the group. This includes the master device from where the grouping was first initiated. Disassociation of a respective member device from the group can be caused by the device being reset, power cycled, or re-associated with a new patient.

7. As previously discussed, if a group has been formed without a patient association, a new patient association can be created from any single device in the group and synchronized across all devices in the group via the association management resource 140.

Further Examples of Grouping Creation and Management

Figure 21:
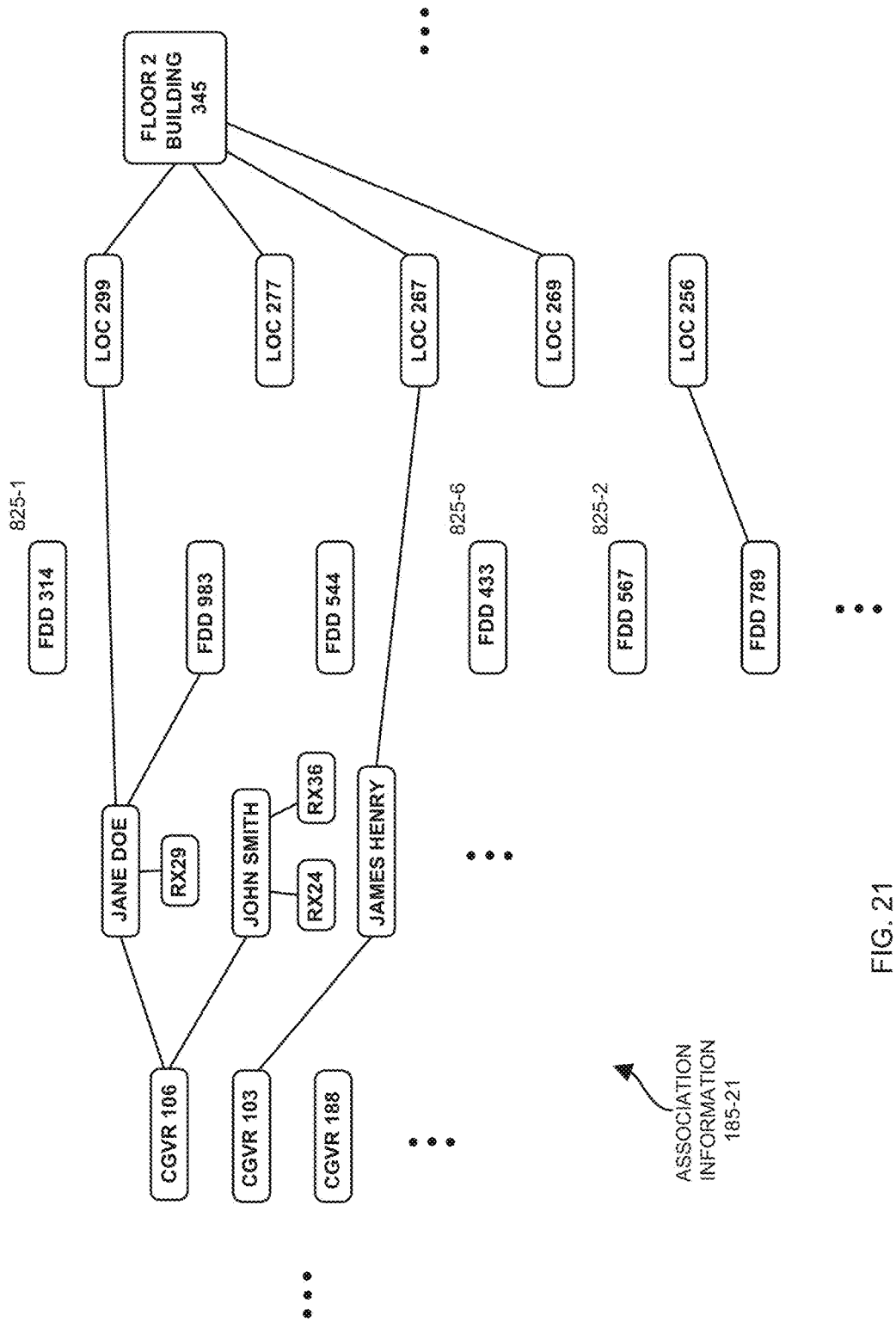
FIG. 21 is an example diagram illustrating association management according to embodiments herein.

FIG. 21 is an example diagram illustrating associations amongst resources according to embodiments herein. Note that each of the medical devices 825 as previously discussed in FIG. 8 can be a fluid delivery system.

As indicated by association information 185-21 in FIG. 21, the medical device 825-1 (FDD 314), medical device 825-6 (FDD 433), and medical device 825-2 (FDD 567) are currently available for use. That is, they are not associated with any patient.

Assume that caregiver 106 creates a respective grouping in any of the manners as discussed above. As previously discussed, the caregiver 106 can operate medical device 825-1 (FDD 314) as a master device to initiate creation of a corresponding grouping.

Figure 22:
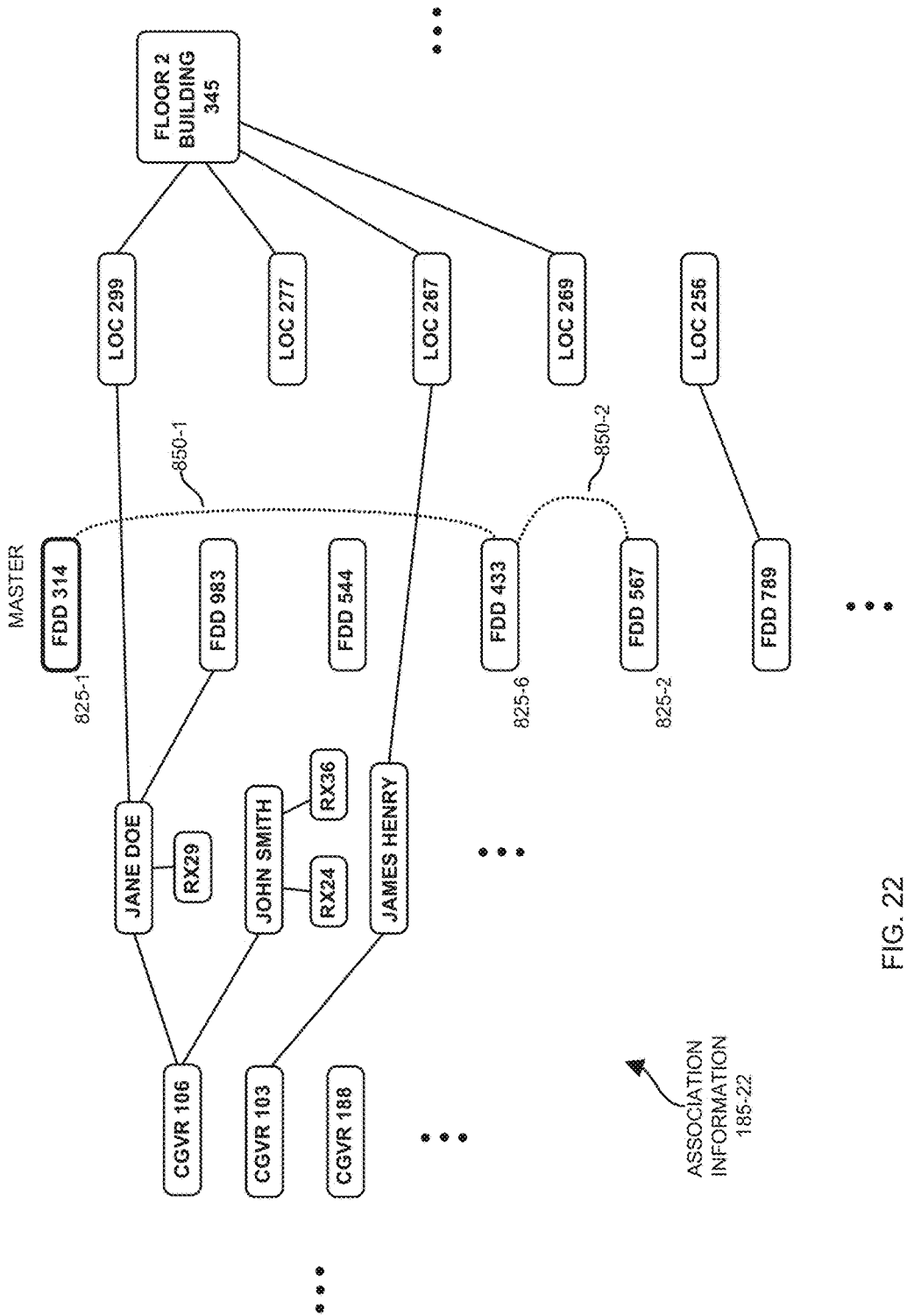
FIG. 22 is an example diagram illustrating creation of assns to indicate a grouping of medical devices according to embodiments herein.

Assume that the caregiver 106 selects medical device 825-2 (FDD 567) and medical device 825-6 (FDD 433) for inclusion in the new grouping. As shown in FIG. 22, in response to receiving notification from the master medical device or the slave medical devices, the association management resource 140 creates a new association 850-1 to indicate the association between the medical device 825-1 (FDD 314) and medical device 825-6 (FDD 433).

In this example embodiment, in response to learning that medical device 825-2 is also to be included in the group, association management resource 140 also creates association 850-2 to indicate that medical device 825-2 is part of the grouping. For example, the association management resource 140 creates new association 850-2 to indicate the association between medical device 825-6 (FDD 433) and medical device 825-2 (FDD 567).

As indicated by association 850-1 and association 850-2 in association information 185-22, it is known that medical device 825-1 (FDD 314), medical device 825-6 (FDD 433), and medical device 825-2 (FDD 567) are all part of the same grouping.

Figure 23:
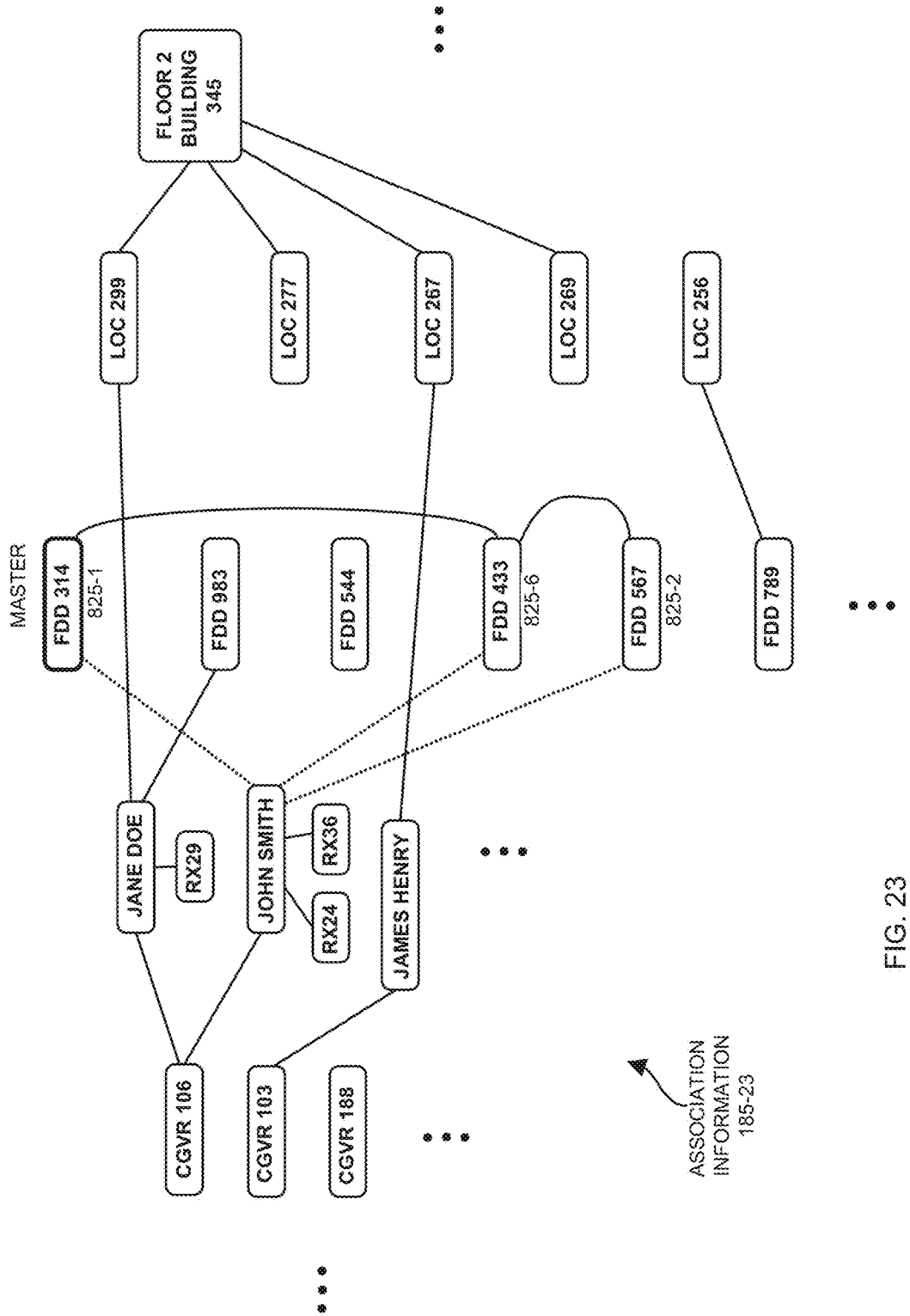
FIG. 23 is an example diagram illustrating association of a grouping of medical devices to a respective patient according to embodiments herein.

After creating a corresponding grouping of related medical devices, the association management resource 140 can receive further input from the corresponding caregiver 106 indicating to associate the grouping of medical devices (FDD 314, FDD 433, and FDD 567) with a corresponding patient's such as John Smith. In response to receiving such input, the association management resource 140 updates the association information 185-23 as shown in FIG. 23 to indicate that the new grouping of medical devices has been associated with recipient 108 (John Smith).

As previously discussed, association of any medical device in the grouping with a corresponding patient results in the whole grouping of medical devices being associated with the corresponding patient. Thus, when the association management resource 140 receives notification that medical device 825-1 (FDD 314) has been assigned by the caregiver 106 to John Smith, the association management resource 140 creates an association between each of the medical devices in the grouping and John Smith as shown.

Figure 24:
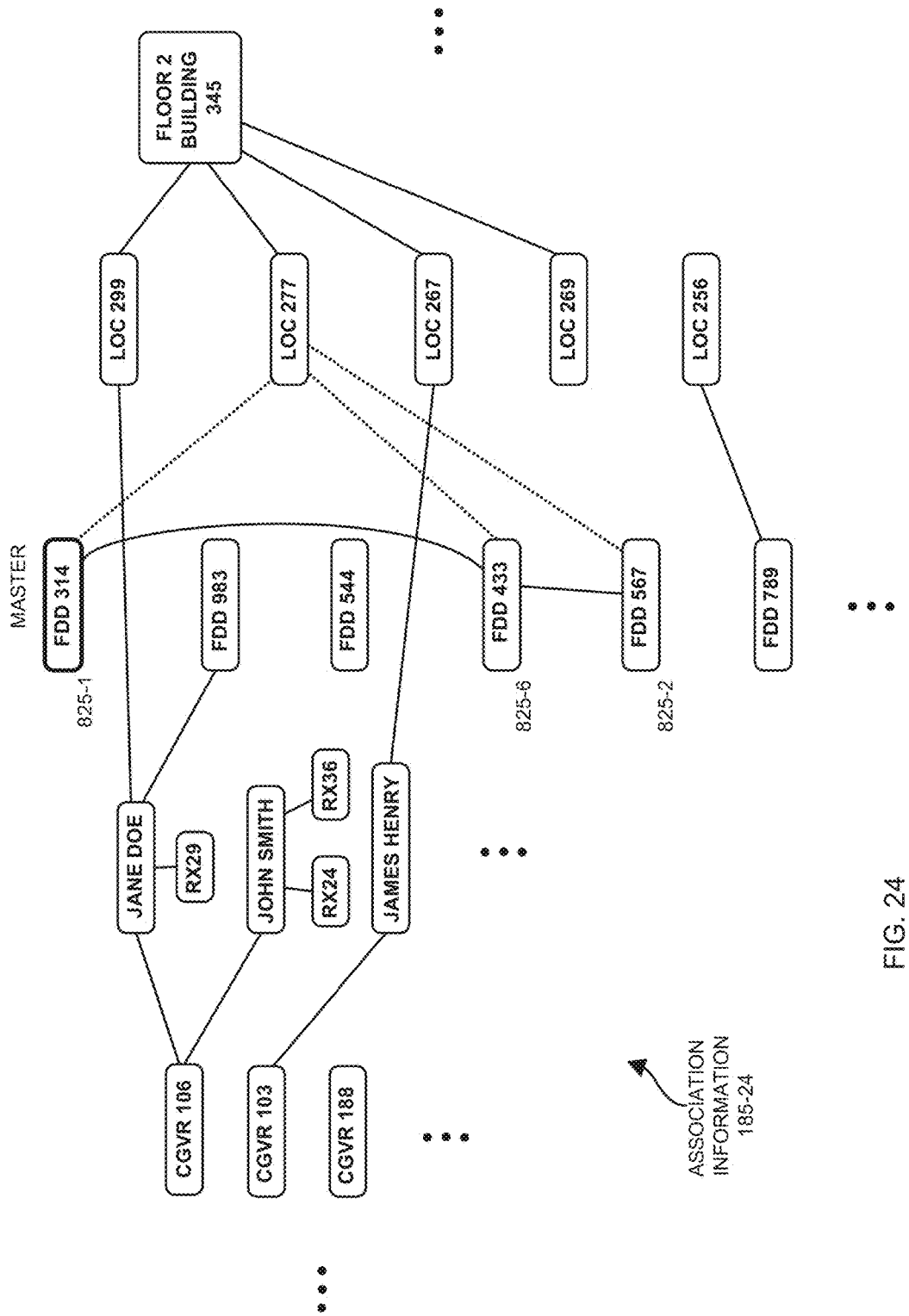
FIG. 24 is an example diagram illustrating association of a grouping of medical devices to a location according to embodiments herein.

In addition to or as an alternative to associating the grouping (FDD 314, FDD 433, and FDD 567) with a corresponding patient, the association management resource 140 can receive input from the caregiver 106 to associate this new grouping with a corresponding location. Assume that the caregiver 106 associates the new grouping of medical devices with domain 150-1 (LOC 277). In response to receiving such input, the association management resource 140 updates the association information 185-24 as shown in FIG. 24 to indicate that the grouping of medical devices has been associated with domain 150-1 (LOC 277).

As previously discussed, association of any medical device in the grouping with a corresponding location results in the whole grouping of medical devices being associated with the corresponding location. Thus, when the association management resource 140 receives notification that medical device 825-1 (FDD 314) has been assigned by the caregiver 106 to domain 150-1 (LOC 277), the association management resource 140 creates an association between each of the medical devices in the grouping and domain 150-1 (LOC 277).

Figure 12:
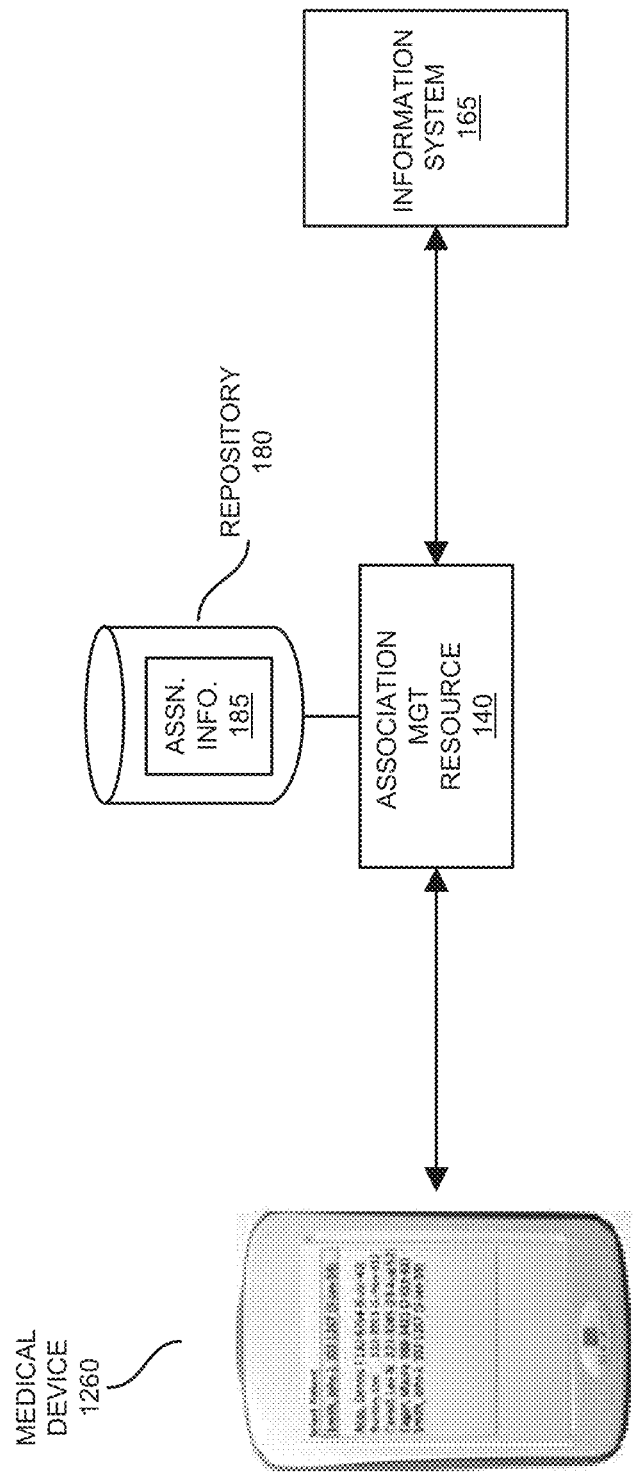
FIG. 12 is an example diagram illustrating census-based association according to embodiments herein.

FIG. 12 is an example diagram illustrating census-based association according to embodiments herein.

Most healthcare enterprises use information systems to track admissions, discharges and transfers across the enterprise. Information systems operating within clinical units across the enterprise can typically both consume ADT (Admit-Discharge-Transfer) messages from the healthcare enterprise and transmit them back to the enterprise when an ADT is initiated from that system. As a device operating within that enterprise, having knowledge of where a patient resides helps that device simplify the association of patients to those devices.

Embodiments herein include a way to provide a medical device 1260 (such as management device 160-1, fluid delivery system 125-1, would delivery system 125-2, etc.) with knowledge of admission, discharge, and transfer information can help facilitate this association process.

Figure 13:
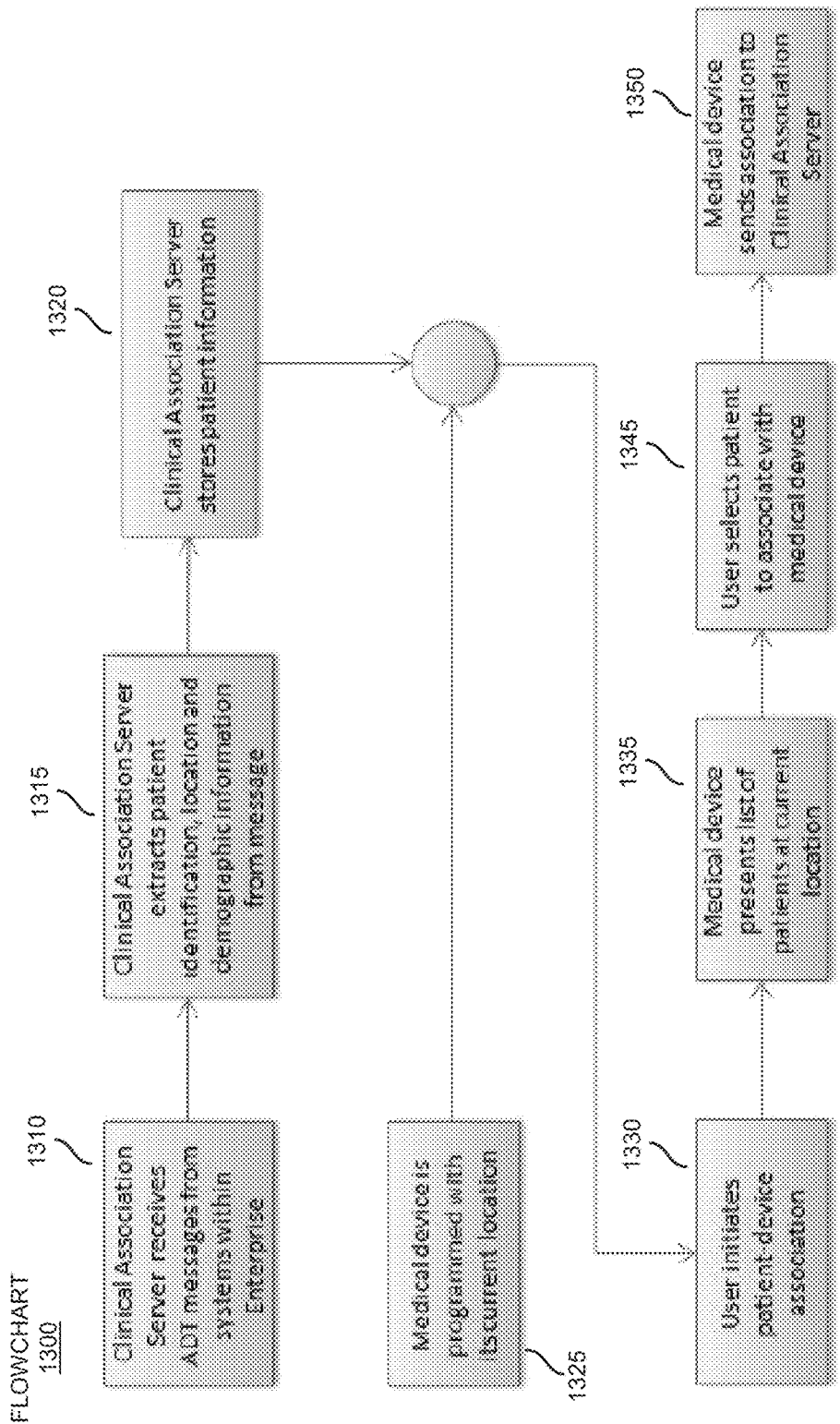
FIG. 13 is an example diagram of a method illustrating census-based association according to embodiments herein.

FIG. 13 is an example diagram illustrating census-based association according to embodiments herein.

As shown in the flowchart 1300, the association management resource can be configured to receive location information associated with one or more entities in the medical environment 100. The association management resource 140 collects location data indicating where each of multiple patients resides in the medical environment 100. The association management resource 140 then stores the associations (such as location data) in repository 180. As previously discussed, each of the associations (such as location data) associates a respective patient with a corresponding location in the medical environment in which the respective patient resides. As previously discussed in FIG. 2, association information 185-1 indicates that John Smith resides that location LOC 277 (such as domain 150-1), Jane Doe resides at location LOC 299, James Henry resides at location LOC 267, etc.

For sake of illustration, in processing block 1310, the association management resource 140 receives messages from information system 165. By way of non-limiting example, the information system 165 can include a healthcare enterprise system that generates messages indicating a location of different entities. In one embodiment, the association management resource 140 receives ADT messages from the information system 165.

In processing block 1315, the association management resource 140 extracts patient identification information, location information, demographic information, etc., from the messages received from information system 165.

In processing block 1320, the association management resource 140 stores the received patient information in repository 180 as association information 185.

In processing block 1325, in a manner as previously discussed, assume that a corresponding medical device 1260 is aware of its current location. The medical device forwards the location information (i.e., it's current location) to association manager resource 140.

Further in a manner as previously discussed, in processing block 1330, the corresponding user operates a respective medical device 1260 such as a fluid delivery system, management device 160-1, etc., to initiate association of the medical device 1260 with a corresponding patient.

Assume that the user requests to associate the medical device 1260 with a corresponding patient. This can include providing input command to the medical device 1260. In response to receiving the request, the medical device 1260 transmits a communication to association manager resource 140 to learn of the patients that are within a vicinity of the current location of the medical device 1260.

Assume that the association management resource 140 receives input indicating that the current location of the medical device 1260 is in a vicinity of floor 2, building 345. Based on association information 185-1 in FIG. 2, the association manager resource 140 detects that Jane Doe, John Smith, and James Henry are present within a vicinity of the medical device. The association manager resource 140 generates a list including these names (i.e., identities of patients) and forwards the list of identities of the patients to the medical device 1260.

In processing block 1335, the medical device 1260 receives the listing of names including Jane Doe, John Smith, and James Henry. The medical device 1260 initiates display of the listing of these names on a respective display screen of the medical device 1260 to indicate patients that were side in a vicinity of the current location of the medical device 1260.

In processing block 1345, the user of the medical device 1260 selects a particular patient (such as John Smith) from the list to associate the medical device 1260 with the particular patient.

In processing block 1350, the medical device 1260 communicates the selection of the particular patient John Smith from the list to association management resource 140. In a manner as previously discussed, the association management resource 140 then creates a new association between the medical device 1260 and the particular patient John Smith.

In accordance with further embodiments, after creating a new association between medical device 1260 (such as management device 160-1, fluid delivery system 125-1, fluid delivery system 125-2, etc.), the operator of the medical device 1260 can generate a query to association management resource 140 to learn of different medication orders that have been assigned to a particular patient John Smith. The caregiver 106 operating the medical device 1260 initiates transmission of a communication from the medical device 1260 to the association management resource 140 to learn of any medication order drugs that have been assigned for delivery to John Smith.

The association management resource 140 receives the inquiry as transmitted over the network 190 from an operator of the medical device 1260 to association management resource 140. As mentioned, the inquiry requests medication order drug information assigned to the particular patient John Smith.

In response to receiving the inquiry, the association management resource 140 searches the association information 185 stored in repository 180 for the medication order drug information assigned to the particular patient John Smith. The association management resource 140 transmits the medication order drug information (associated with RX24 and RX36) over the network 190 to the operator of the medical device. The medical device 1260 initiates display of the medication order drug information on a display screen of the medical device for viewing by the respective caregiver 106.

Note again that retrieval of the medication order drug information associated with John Smith is shown by way of non-limiting example only. Subsequent to creating the association between the medical device 1260 and a corresponding patient (or other entity), the operator of the medical device 1260 can obtain other types of information associated with the corresponding patient such as a doctor that has been assigned to the patient, the history of medical information associated with the patient, etc.

Figure 14:
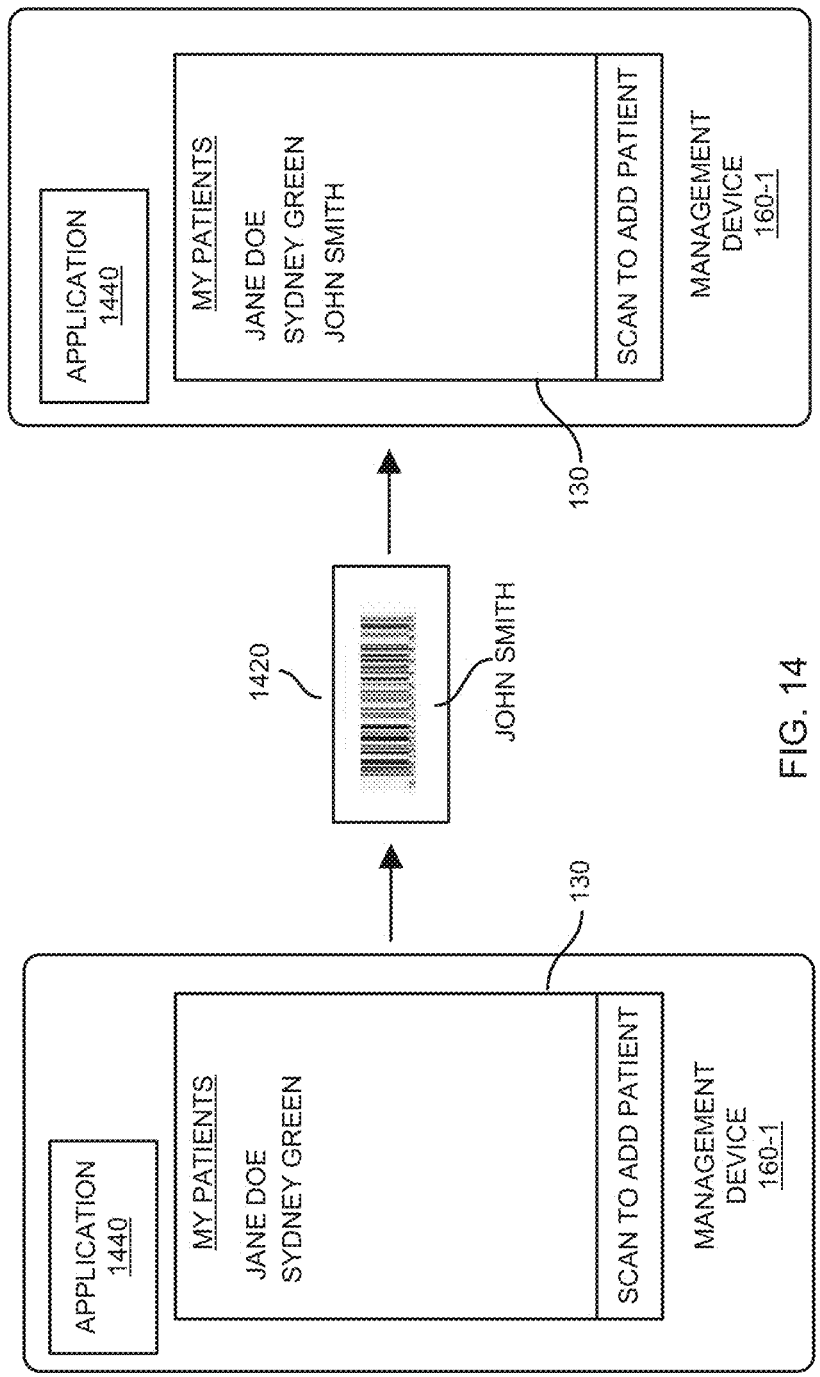
FIG. 14 is an example diagram illustrating use of a management device to associate patients to a particular caregiver according to embodiments herein.

FIG. 14 is an example diagram illustrating use of a management device to manage medical care according to embodiments herein.

Mobile devices ranging from laptops to cell phones are increasingly becoming the primary productivity tool of care providers throughout the healthcare enterprise. The same devices (such as management device 160-1) therefore become the ideal host for software applications enabling care providers to associate themselves with their patients and associate their patients with connected medical devices.

The management device 160-1 can be any suitable type of computing device such as a smartphone, scanner, PDA, tablet computer, laptop computer, etc.

Recall that management device 160-1 is disparately located with respect to fluid delivery systems or other medical devices located in the medical environment 100. In one embodiment, the caregiver 106 stores the management device 160-1 in their pocket when moving from one location to another.

Management device 160-1 executes management application 1440. Execution of management application 1440 enables the caregiver to define or create associations as part of their normal care workflow.

The management application 1440 can be configured to perform any suitable type of operations such as receiving input from a corresponding caregiver 106 operating the management device 160-1, providing notifications to the corresponding caregiver 106, communicating with association management resource 140, and so on.

As previously discussed, the caregiver 106 can operate management device 160-1 in order to associate itself with a corresponding patient. For example as previously discussed, the management device 160-1 can be configured to transmit its corresponding location information to association management resource 140. Using association information 185, the association management resource 140 forwards the listing of patients in a nearby vicinity of the management device 160-1 to management device 160-1 for display on display screen 130. If desired, the caregiver 106 can provide input indicating which of the patients the caregiver 106 is going to provide care.

Another way of associating a particular caregiver to a patient is to scan a corresponding barcode 1420 associated with the patient. For example, assume that caregiver 106 has already created an association with Jane Doe and Sidney Green indicating that the caregiver 106 will be providing care to these patients.

The caregiver 106 can operate the management device and scan the barcode 1420 associated with John Smith to add John Smith as a patient cared for by caregiver 106. In response to scanning the barcode 1420, the management device 160-1 adds John Smith to the displayed list of patients that are cared for by the corresponding caregiver 106.

In accordance with further embodiments, in response to scanning of the barcode 1420, the application 1440 transmits an identity of the scanned patient to association management resource 140. The association management resource 140 updates the association information 185 to indicate that the caregiver 106 is now assigned to provide care to patient John Smith. As previously discussed, updating of the association information 185 can include creating an association between caregiver 106 (CGVR106) and John Smith.

After creating the associations between the caregiver and a set of patients such as Jane Doe, Sidney Green, and John Smith, the caregiver 160-1 can operate the management device 160-1 to determine which patients are assigned to the caregiver 106. For example, the caregiver 106 can generate a message from management device 160-1 to association management resource 140 to learn of any patients that are assigned to the caregiver 106. The association management resource 140 transmits the list to management device 160-1 for display to caregiver 106.

Accordingly, the association management resource 140 can be configured to: receive a communication transmitted over the network 190 from the management device 160-1 (mobile device) operated by the caregiver 106, the communication requesting a listing of patients assigned to the caregiver; analyze the association information 185 identifying a set of patients assigned to the caregiver; and in response to receiving the second communication, transmit a reply message over the network 190 to the management device 160-1 operated by the caregiver 106, the reply message indicating the set of patients assigned to the caregiver 106.

Figure 15:
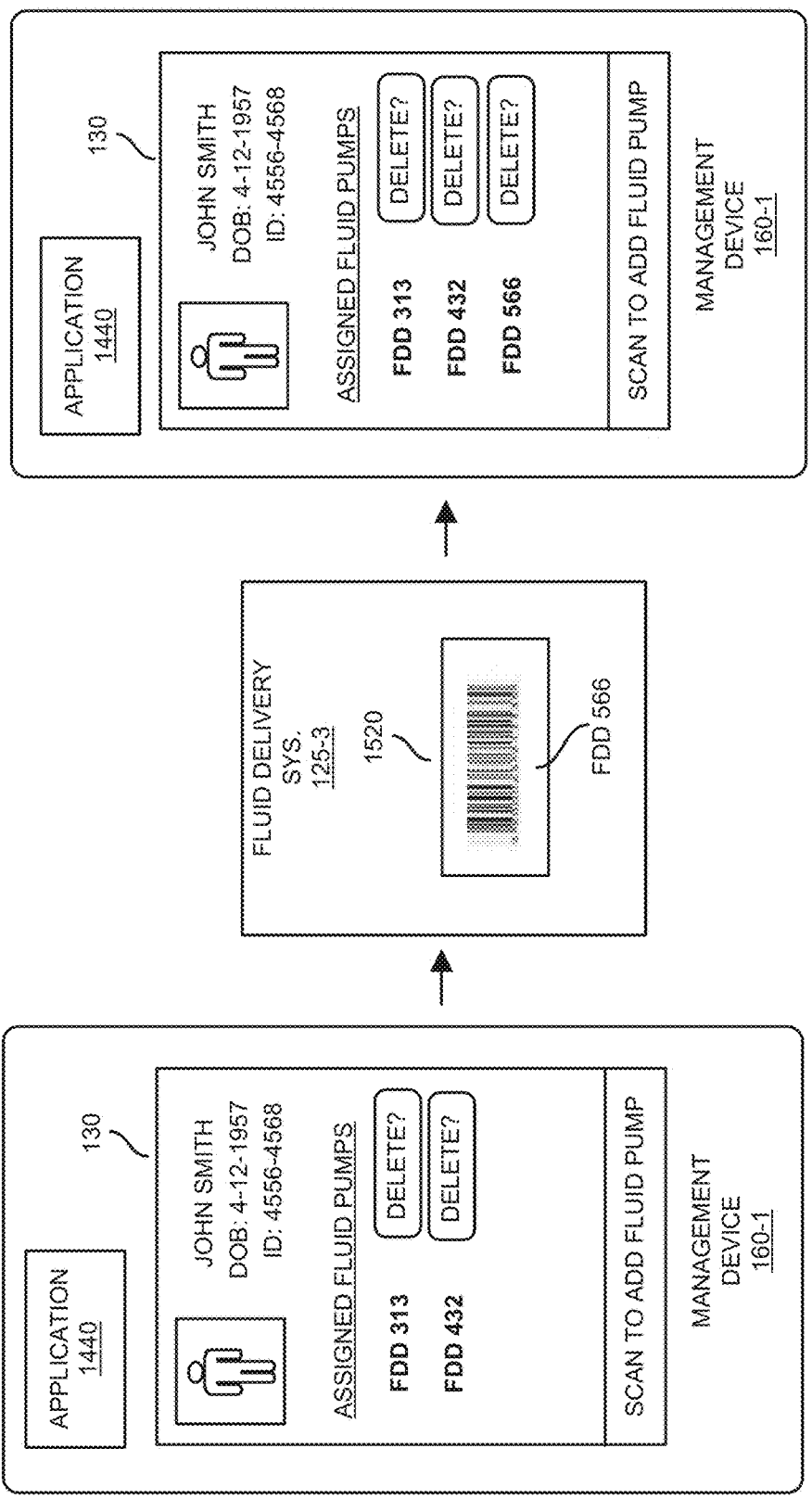
FIG. 15 is an example diagram illustrating use of a caregiver's management device to associate one or more medical devices with a corresponding patient according to embodiments herein.

FIG. 15 is an example diagram illustrating use of a caregiver's management device to associate one or more fluid delivery systems with a corresponding patient according to embodiments herein.

Subsequent to associating patient John Smith to the caregiver 106, the caregiver 106 can operate the management device 160-1 to identify any medical devices that have been assigned to the corresponding patient John Smith.

For example, the caregiver 106 can operate management device 160-1 to communicate over network 190 with the association management resource 140 and retrieve a listing of any medical devices (such as fluid pumps) that have been assigned to the corresponding patient John Smith. The patient John Smith can be selected from the display screen 130 in FIG. 14 listing patients Jane Doe, Sidney Green, and John Smith.

The association management resource 140 receives the communication transmitted over the network 190 from the management device 160-1 operated by the caregiver 106. The communication indicates selection of a particular patient such as John Smith.

In response to receiving the communication from management device 160-1 for any medical devices assigned to John Smith, the association management resource 140 transmits a message over the network 190 to the management device 160-1 operated by the caregiver 160-1. The reply message from the association management resource 140 includes a listing of medical devices such as fluid delivery systems assigned to the particular patient John Smith.

In this example embodiment, assume that the association management resource 140 indicates that fluid delivery system 125-1 (FDD 313) and fluid delivery system 125-2 (FDD 432) both have been assigned for use by John Smith. As shown in FIG. 15, the management device 160-1 initiates display of the different fluid pumps assigned for use by John Smith.

As further shown in FIG. 15, the caregiver 106 operating management device 160-1 can be configured to scan barcode 1520 located on the fluid delivery system 125-3. Scanning of the barcode 1520 indicates that the caregiver 106 like to add the fluid delivery system 125-3 (FDD 566) for use by John Smith. The management device 160-1 communicates this information to association management resource 140.

In response to assigning the fluid delivery system 125-3 to the patient John Smith, the management device 160-1 initiates display of the identity of the fluid delivery system 125-3 (FDD 566) on the corresponding display screen 130 of management device 160-1 to indicate that the fluid delivery system 125-3 is now assigned for use by John Smith.

Figure 16:
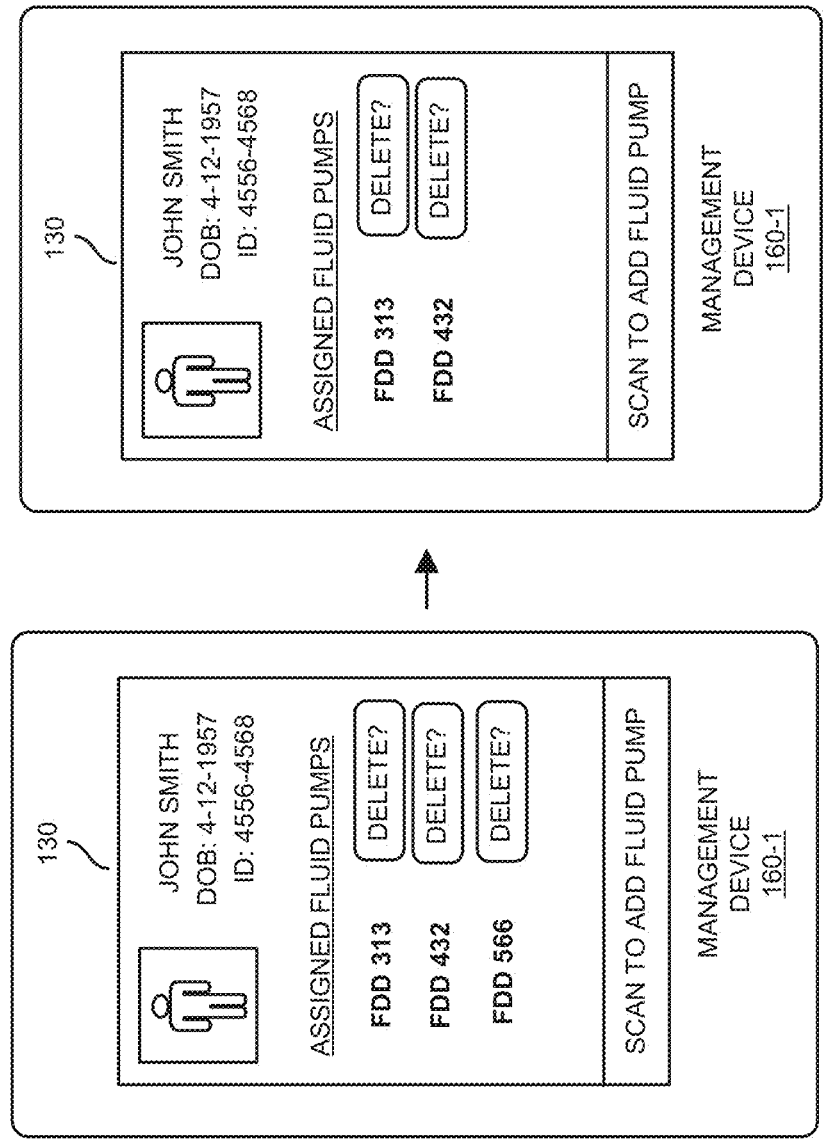
FIG. 16 is an example diagram illustrating use of a caregiver operated management device to dissociate a medical device from a corresponding patient according to embodiments herein.

FIG. 16 is an example diagram illustrating use of a caregiver operated management device to dissociate a fluid delivery system with a corresponding patient according to embodiments herein.

As shown, the management device 160-1 displays the different fluid delivery systems that have been assigned for use by John Smith.

For example, fluid delivery system 125-1 (FDD 313), fluid delivery system 125-2 (FDD 432), and fluid delivery system 125-3 (FDD 566) have been assigned for use by John Smith. In response to receiving selection of delete symbol 1620 displayed on display screen 130 of management device 160-1, management device 160-1 communicates with association management resource 140 to delete a respective association between delivery system 125-3 (FDD 566) and John Smith.

Association management resource 140 receives the communication and updates the association information 185 to indicate that the association between fluid delivery system 125-3 (FDD 566) and John Smith has been terminated. The association management resource 140 communicates the termination of the association to management device 160-1.

Subsequent to terminating the association, the management device 160-1 updates its corresponding display screen to indicate that only fluid delivery system 125-1 (FDD 313) and fluid delivery system 125-2 (FDD 432) are assigned for use by patient John Smith.

Figure 17:
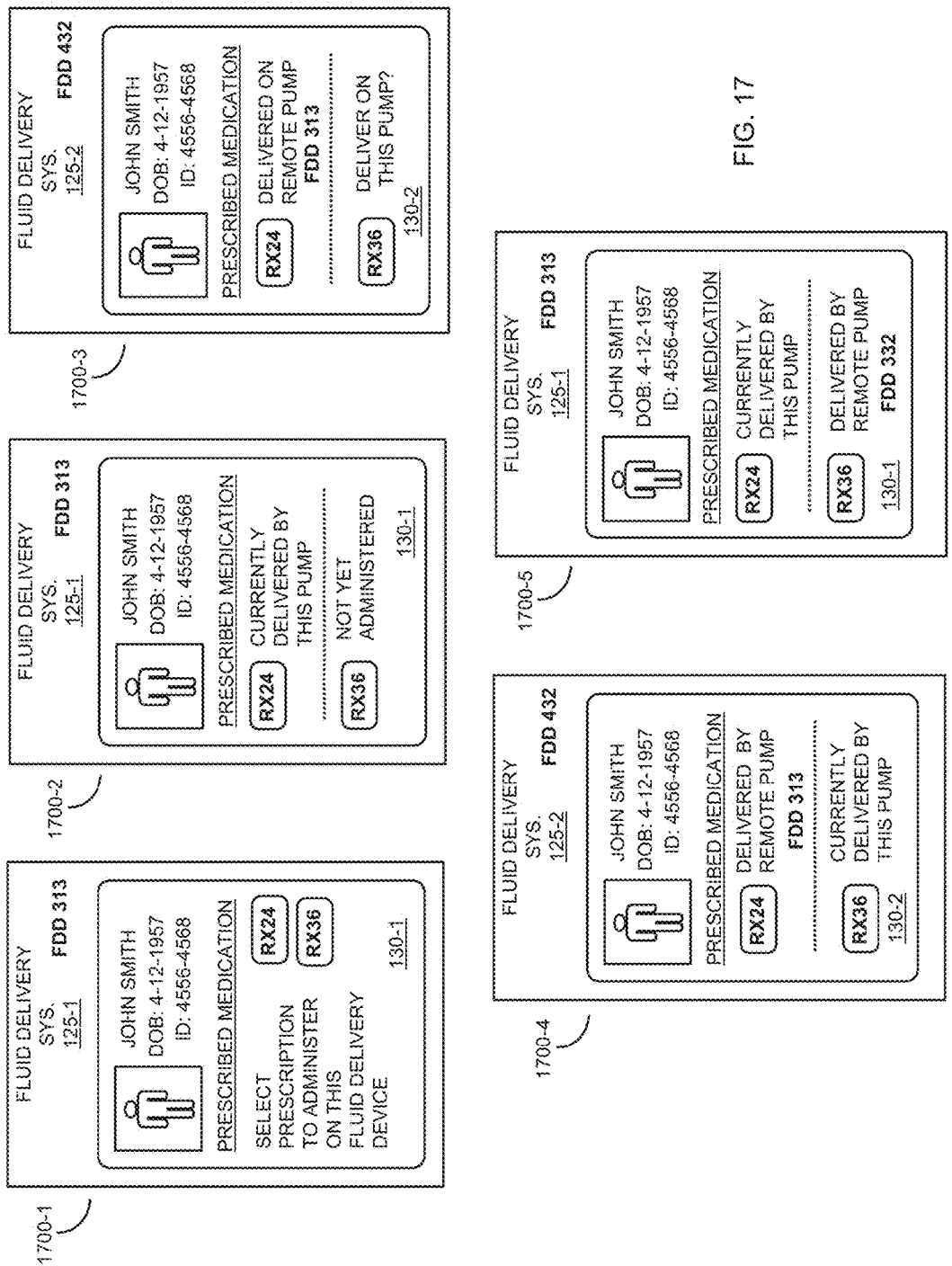
FIG. 17 is an example diagram illustrating use of association information to facilitate delivery of multiple fluid-based drugs to a patient using multiple fluid delivery systems according to embodiments herein.

FIG. 17 is an example diagram illustrating use of association information to facilitate delivery of multiple fluid-based drugs to a patient using multiple fluid delivery systems according to embodiments herein.

In accordance with embodiments herein, medical devices that are involved in the delivery of a medication benefit from having access to the order for that medication over network 190. For example, after an association is created between a patient and a device, the patient's order (such as a object specifying parameters of delivering a medication order) may be forwarded from association management resource 140 over network 190 to the respective medical device that is assigned to deliver the medication order fluid to a corresponding recipient.

The following states illustrate settings of corresponding fluid delivery systems during the process of assigning different fluid-based drugs by a particular fluid delivery system. The process of receiving input from the different fluid delivery systems and display of corresponding notification information makes it easier for a corresponding caregiver to safely administer different drugs from multiple fluid pumps.

State 1700-1:

Assume in this example embodiment that the caregiver 106 operates the fluid delivery system 125-1 to identify medication order medication assigned for delivery to patient John Smith. In such an instance, the caregiver 106 operates fluid delivery device 125-1 to transmit a query to association management resource 140 to learn of medication order medication prescribed to patient John Smith. In one embodiment, the query from the caregiver 106 includes a request for a listing of medicine prescribed to the patient John Smith.

In response to receiving the query, the association management resource 140 searches the association information 185 and repository 180 for medication orders assigned to John Smith. Association management resource 140 analyzes the association information 185 and determines that medication order RX 24 and RX 36 have been assigned to John Smith. The association management resource 140 transmits a message (including medical information) to fluid delivery system 125-1. The medical information in the message received by fluid delivery system 125-1 indicates that John Smith has been assigned medication order drugs RX 24 and RX 36.

Fluid delivery system 125-1 initiates display of a notification on display screen 130-1 of fluid delivery system 125-1 that both RX 24 and RX36 are to be administered to patient John Smith. Assume in this example that the caregiver 106 operating the fluid delivery system 125-1 selects medication order RX 24 for delivery by fluid delivery system 125-1. Selection of medication order RX 24 can include touching a display of a symbol RX24 on the display screen of fluid delivery system 125-1.

In one embodiment, in response to receiving selection of the symbol RX24 on the display screen of the fluid delivery system 125-1, the fluid delivery system 125-1 transmits a message to association management resource 140 to indicate that the fluid delivery system 125-1 has been selected to deliver the medication order RX24 to patient John Smith. In response to receiving the input, and in a manner as previously discussed, the association management resource 140 creates a new association between fluid delivery system 125-1 (FDD 313) and node RX 24 in association information 185 to indicate that the medication order RX 24 is being administered by the fluid delivery system 125-1.

State 1700-2:

In response to receiving input indicating that fluid delivery system 125-1 has been selected to deliver medication order RX 24 to the patient John Smith, the fluid delivery system 125-1 presents a notification on a respective display screen of fluid delivery system 125-1 that medication order RX 24 has been assigned for delivery by fluid delivery system 125-1. If desired, as shown, the display screen 130-1 of fluid delivery system 125-1 can further indicate that medication order RX 36 is still outstanding. For example, the message "NON YET ADMINISTERED" or other visual indicator implies that medication order RX 36 has not yet been assigned for delivery by a particular fluid delivery system.

State 1700-3:

Further embodiments herein can include providing notification to fluid delivery system 125-2 that the corresponding medication order RX 24 is being delivered to the recipient 108 (John Smith) via fluid delivery system 125-1 (FDD 313). For example, in one embodiment, the fluid delivery system 125-2 receives notification from association management resource 140 or other suitable resource that the fluid delivery system 125-1 has been assigned to administer the medication order RX 24 to patient John Smith. In response to receiving such notification, the fluid delivery system 125-2 initiates display of a message on display screen 130-2 indicating that the medication order RX24 is being delivered on remote fluid delivery system 125-1 (FDD 313). Accordingly, via the notification displayed on fluid delivery system 125-2, the caregiver 106 is able to determine that the medication order RX 36 has not yet been assigned for delivery by a respective fluid pump.

Assume that the carrier 106 provides input to fluid delivery system 125-2 indicating selection of medication order RX36 for delivery to the patient via fluid delivery system 125-2. In one embodiment, the caregiver 106 touches the symbol labeled RX36 on display screen fluid delivery system 125-2 in order to assign delivery system 125-2 for delivery of the medication order RX 36.

In response to receiving the assignment of medication order RX 36 to fluid delivery system 125-2, the fluid delivery system 125-2 communicates with the association management resource 140. In response the notification, the association management resource 140 creates an association between medication order RX 36 and the fluid delivery system 125-2 (FDD 432) to indicate that fluid delivery system 125-2 has been configured to deliver the medication order RX 36. Accordingly, via this newly created association, association management resource 140 tracks that the fluid delivery system 125-2 has been assigned to deliver medication order RX 36.

State 1700-4:

In response to the assignment of delivering medication order RX 36 on fluid delivery system 125-2, the fluid delivery system 125-2 updates its corresponding display screen 130-2 to indicate that medication order RX 36 has been assigned for delivery on fluid delivery system 125-2.

State 1700-5:

Further embodiments herein can include providing notification to fluid delivery system 125-1 that the fluid delivery system 125-2 has been assigned to deliver medication order RX 36 to recipient 108 (John Smith). Fluid delivery system 125-1 can be configured to receive the notification from any suitable resource such as from fluid delivery system 125-2 or from association management resource 140 to update display screen 130-1.

Further embodiments herein can include receiving feedback from each of the fluid delivery systems indicating a status of delivering a corresponding medication order. For example, during the course of delivering medication order RX 24, the fluid delivery system 125-1 can be configured to continuously communicate status information back to association management resource 140 regarding progress of delivering the medication order RX24 to patient John Smith. In a similar manner, during the course of delivering medication order RX36, the fluid delivery system 125-2 can be configured to continuously communicate status information back to association management resource 140 regarding progress of delivering the medication order RX36 to patient John Smith.

Feedback from a respective fluid delivery system can include information such as a time when the medication order is administered, amounts of the medication order that have not yet been delivered to a corresponding patient, etc.

In one embodiment, the caregiver 106 operates the medical device 160-1 to retrieve the status information associated with delivery of the medication order drugs from association management to resource 140. Accordingly, from a remote location, the carrier 106 can monitor attributes of the fluid delivery systems 125-1 and 125-2.

Figure 18:
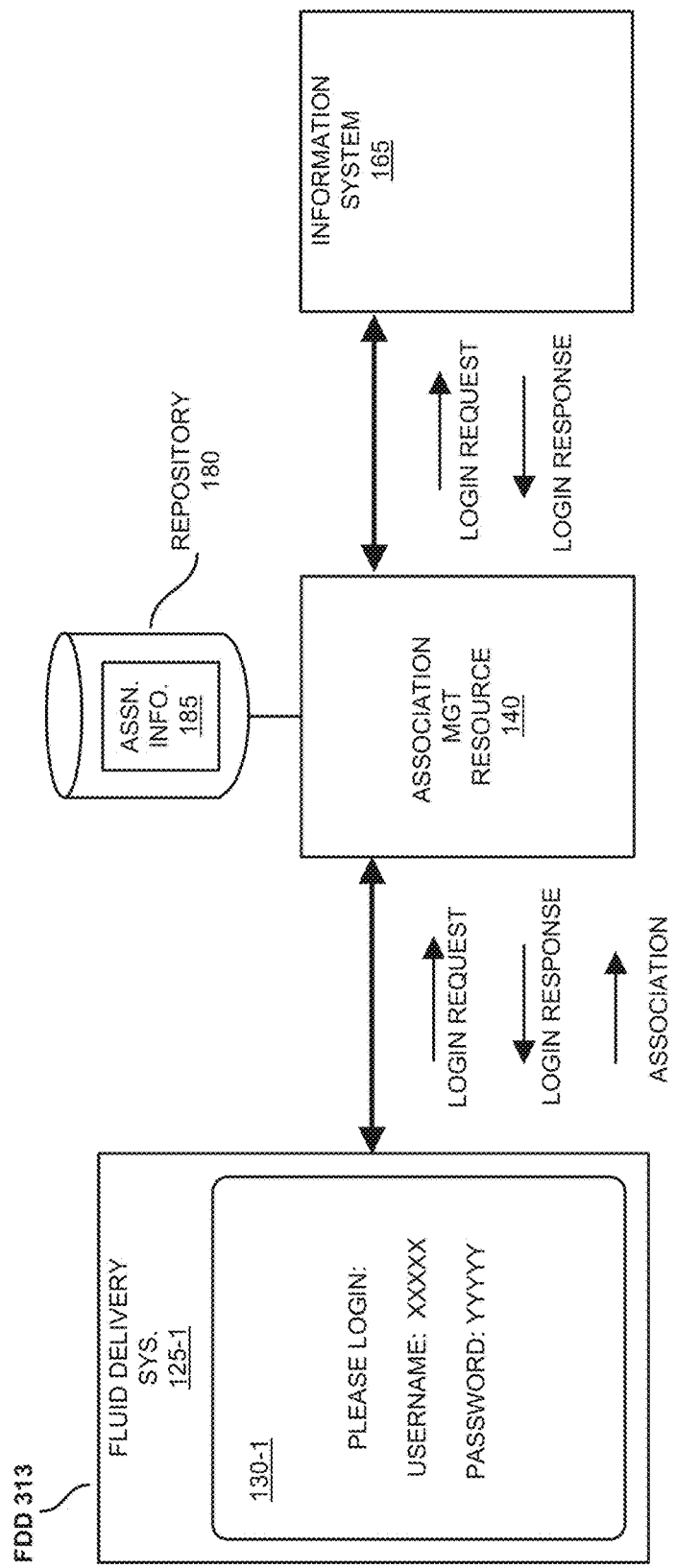
FIG. 18 is an example diagram illustrating authentication and authorization of a user of a medical device according to embodiments herein.

FIG. 18 is an example diagram illustrating authentication and authorization of a user of a fluid delivery system according to embodiments herein.

User authentication and authorization can be managed centrally within a healthcare enterprise. Information system 165 can include technology such as Microsoft's Active Directory, to manage user accounts (which include details on a user's credentials), roles, permissions, etc.

In one embodiment, information system 165 includes an enterprise user management system. The association management resource 140 (clinical association server) is capable of interacting with an enterprise user management system and using that system to authenticate and authorize a user attempting to log into one of its connected medical devices. Optionally, the medical device operated by a respective caregiver is capable of interacting directly with an enterprise user management system and using that system to authenticate and authorize a user attempting to log into itself.

As a more specific example, assume that caregiver 106 would like to log onto fluid delivery system 125-1. In one embodiment, the fluid delivery system 125-1 initiates a challenge to a caregiver 106 operating the fluid delivery system to provide appropriate authentication information (such as username and password information) to operate the fluid delivery system 125-1.

In response to receiving input from a caregiver 106 desiring to log onto fluid delivery system 125-1, the fluid delivery system 125-1 transmits the login request (such as username and password information) S inputted by the caregiver 106 to association management resource 140. Association management resource 140 forwards the login request to information system 165 (such as an enterprise user management system). Thus, in response to the challenge, the information system 165 receives (such as login request) over the network 190 from the caregiver 106. As mentioned, the login requests can include authentication information (such as username and password) to operate fluid delivery system 125-1.

The information system 165 or other suitable resource verifies the authentication information received from the fluid delivery system 125-1.

Subsequent to verifying the authentication information provided by the caregiver 106 in the login request, the information system 165 transmits a login response (such as a command) to association management resource 140. The association management resource 140 forwards the login response to fluid delivery system 125-1. The login response (such as a command) enables (e.g., unlocks) the fluid delivery system 125-1, enabling the caregiver to perform operations as discussed herein such as deliver fluid to a patient using the fluid delivery system 125-1.

In accordance with further embodiments, and as previously discussed, after the caregiver 106 has logged in and is enabled to operate fluid delivery system 125-1, the caregiver 106 can further communicate with association management resource 140 in order to associate the fluid delivery system 125-1 to the caregiver 106. In other words, as previously discussed, the caregiver 106 can provide input specifying an identity of the caregiver 106 to the association management resource 140. The association management resource 140 then modifies association information 185 to create an association between the caregiver 106 and the fluid delivery system 125-1.

In one embodiment, medical device (fluid delivery system 125-1) has the ability to cache previously authenticated users, and optionally utilize that cache to authenticate users when the server is unable to provide user authentication and/or authorization services. Thus, the user can be authenticated without having to communicate over network 190 with a remote resource such as information system 165 or association management resource 140.

As mentioned, medical device (such as fluid system 125-1) provides the logged in user the ability to indicate their association with the medical device and the patient being treated.

In one embodiment, after an association has been established between a caregiver 106 and the corresponding medical device (such as a fluid delivery system), all data generated by a respective fluid delivery system, such as medical alarms, can be tagged with an identity of the caregiver 106. This information is optionally routed to the caregiver 106 for display on medical device 160-1.

Figure 19:
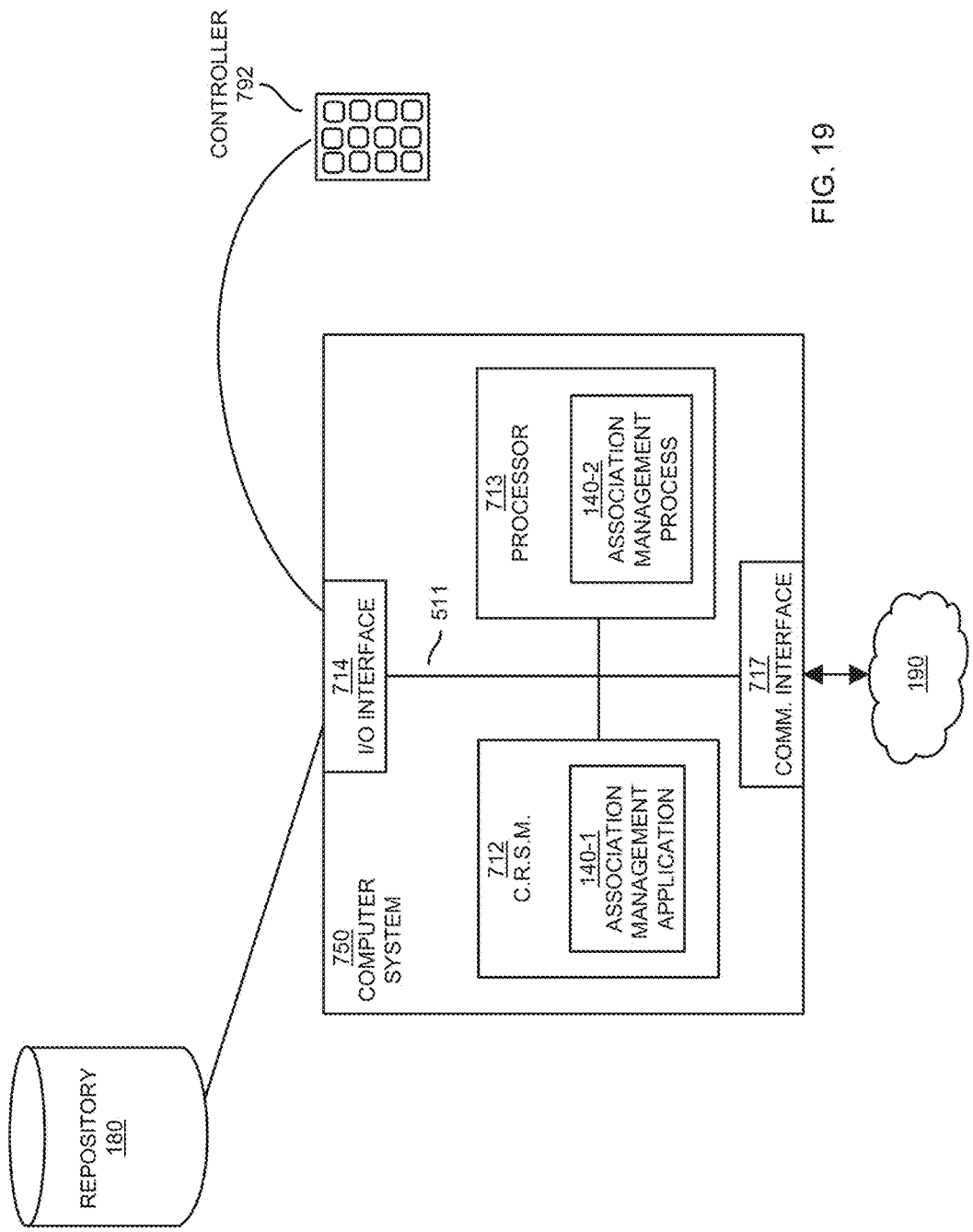
FIG. 19 is a diagram illustrating an example computer architecture in which to execute any of the functionality according to embodiments herein.

FIG. 19 is an example block diagram of a computer device for implementing any of the operations as discussed herein according to embodiments herein.

In one embodiment, fluid delivery system 100 includes a computer system 750 to execute association management resource 140, management application 1440, etc.

As shown, computer system 750 of the present example includes an interconnect 711, a processor 713 (such as one or more processor devices, computer processor hardware, etc.), computer readable storage medium 712 (such as hardware storage to store data), I/O interface 714, and communications interface 717.

Interconnect 711 provides connectivity amongst processor 713, computer readable storage media 712, I/O interface 714, and communication interface 717.

I/O interface 714 provides connectivity to a repository 780 and, if present, other devices such as a playback device, display screen, input resource 792, a computer mouse, etc.

Computer readable storage medium 712 (such as a non-transitory hardware medium) can be any hardware storage resource or device such as memory, optical storage, hard drive, rotating disk, etc. In one embodiment, the computer readable storage medium 712 stores instructions executed by processor 713.

Communications interface 717 enables the computer system 750 and processor 713 to communicate over a resource such as network 190 to retrieve information from remote sources and communicate with other computers. I/O interface 714 enables processor 713 to retrieve stored information from repository 180.

As shown, computer readable storage media 712 is encoded with controller application 140-1 (e.g., software, firmware, etc.) executed by processor 713. Controller application 140-1 can be configured to include instructions to implement any of the operations as discussed herein.

During operation of one embodiment, processor 713 (e.g., computer processor hardware) accesses computer readable storage media 712 via the use of interconnect 711 in order to launch, run, execute, interpret or otherwise perform the instructions in association management application 140-1 stored on computer readable storage medium 712.

Execution of the association management application 140-1 produces processing functionality such as association management process 140-2 in processor 713. In other words, the association management process 140-2 associated with processor 713 represents one or more aspects of executing association management application 140-1 within or upon the processor 713 in the computer system 750.

Those skilled in the art will understand that the computer system 750 can include other processes and/or software and hardware components, such as an operating system that controls allocation and use of hardware resources to execute association management application 140-1.

In accordance with different embodiments, note that computer system may be any of various types of devices, including, but not limited to, a wireless access point, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. In one non-limiting example embodiment, the computer system 850 resides in fluid delivery system 100. However, note that computer system 850 may reside at any location or can be included in any suitable resource in network environment 100 to implement functionality as discussed herein.

Functionality supported by the different resources will now be discussed via flowcharts in FIG. 20. Note that the steps in the flowcharts below can be executed in any suitable order.

Figure 20:
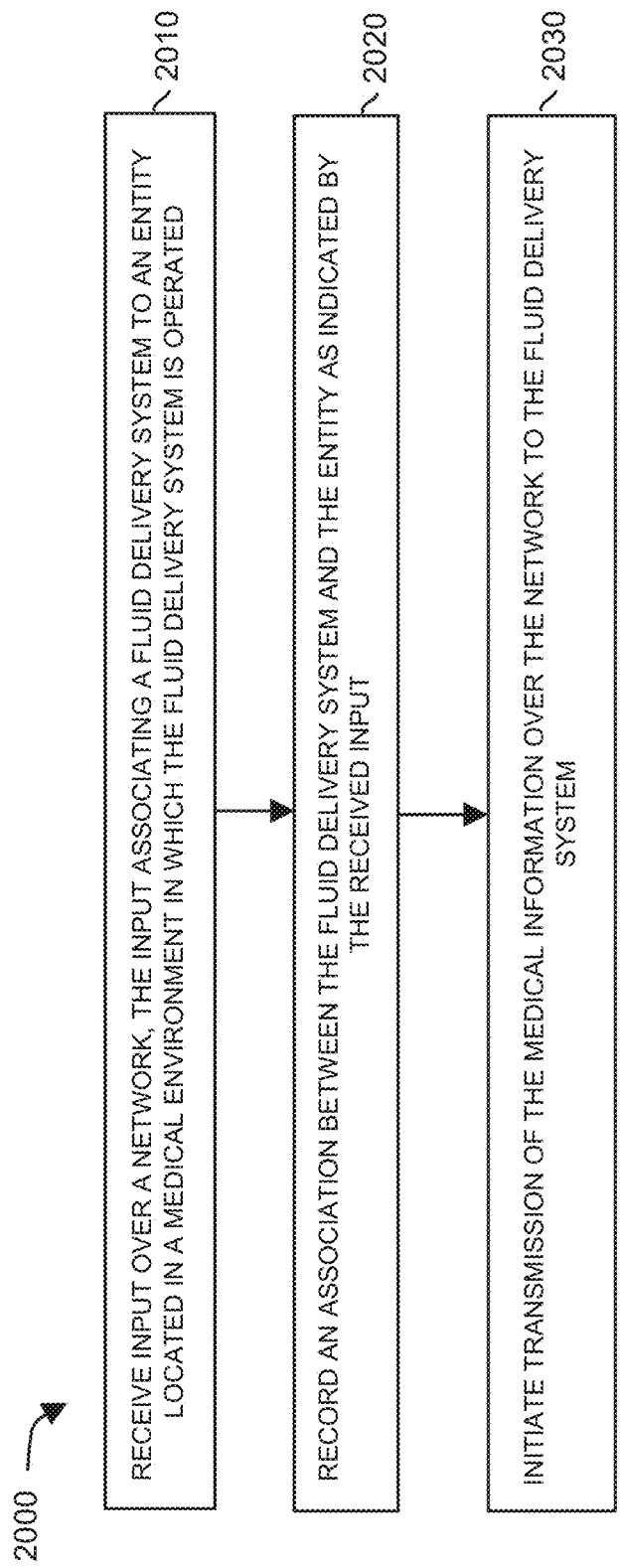
FIG. 20 is an example diagram illustrating a method facilitating association of a medical device to a corresponding entity according to embodiments herein.

FIG. 20 is a flowchart 2000 illustrating an example method according to embodiments. Note that there will be some overlap with respect to concepts as discussed above.

In processing block 2010, the association management resource 140 receives input over a network 190. The input associates fluid delivery system 125-1 to an entity located in a medical environment 100 in which the fluid delivery system 125-1 is operated.

In processing block 2020, the association management resource 140 records an association between the fluid delivery system 125-1 and the entity as indicated by the received input.

In processing block 2030, the association management resource 140 initiates transmission of medical information associated with the entity over the network to fluid delivery system 125-1.

Note again that techniques herein are well suited for use in management of fluid delivery systems. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. In a network environment including a master device, a second fluid delivery device and a third fluid delivery device, a method comprising:
via computer processor hardware, performing operations of:
initiating a group of the master device, second fluid delivery device, and the third fluid delivery device by the master device transmitting a broadcast message with an invitation to the second fluid delivery device and the third fluid delivery device, wherein the invitation comprises an identifier for the master device;
receiving the invitation by the second fluid delivery device and the third fluid delivery device and prompting a user to acknowledge the invitation;
displaying the invitation by the second fluid delivery device and the third fluid delivery device that the master medical device generated for the second fluid delivery device and the third fluid delivery device to join and initiate formation of the group,
wherein the identifier for the master device and an identifier for the second fluid delivery device and the third fluid delivery device is stored in a memory,
receiving input over a network or the group interconnecting the second fluid delivery device and the third fluid delivery device, the input associating the third fluid delivery device to the second fluid delivery device, the third fluid delivery device located in a medical environment in which the second fluid delivery device is operated;
based on the input, recording an association between the third fluid delivery device and the second fluid delivery device, the association indicating assignment of both the second fluid delivery device and the third fluid delivery device for use by the patient;
based on the recorded association, initiating transmission of a message to the third fluid delivery device, the message including medical information indicating that the second fluid delivery device delivers a first fluid to the patient;
initiating display of the medical information as indicated by the message on a display screen of the third fluid delivery device, the third fluid delivery device operated by a caregiver of the patient, display of the medical information on the display screen of the third fluid delivery device indicating to the caregiver of the patient that the second fluid delivery device is used to deliver the first fluid to the patient; and
in response to receiving a fluid delivery selection by the caregiver operating the third fluid delivery device, controlling delivery of a second fluid to the patient from the third fluid delivery device.

2. The method as in claim 1, wherein initiating transmission of the message to the third fluid delivery device includes communicating the message over a wireless communication link to the third fluid delivery device.

3. The method as in claim 1, wherein the medical information is associated with the second fluid delivery device prior to receiving the input over the network to associate the third fluid delivery device to the second fluid delivery device, the method further comprising:
receiving the input from the third fluid delivery device, the input generated by the caregiver operating the third fluid delivery device; and
wherein initiating transmission of the medical information over the network includes communicating the medical information to the third fluid delivery device in response to receiving a search query from the caregiver for the medical information associated with the second fluid delivery device.

4. The method as in claim 1, wherein the second fluid delivery device includes a fluid pump, the fluid pump controlled by the second fluid delivery device to deliver the first fluid to the patient; and
wherein the third fluid delivery device includes an other fluid pump, the other fluid pump controlled by the third fluid delivery device to deliver the second fluid to the patient.

5. The method as in claim 1 further comprising:
initiating communication with a set of multiple medical devices located in a vicinity of the second fluid delivery device, the third fluid delivery device included in the multiple medical devices;
providing notification to the caregiver operating the second fluid delivery device, the notification indicating that the set of multiple medical devices is available in a vicinity of the second fluid delivery device.

6. The method as in claim 5, wherein providing the notification includes:
activating a corresponding prompt at each respective medical device in the set, the activated corresponding prompt indicating that the respective medical device can be programmed to join a group including the second fluid delivery device.

7. The method as in claim 5, wherein providing the notification includes:
initiating display of a message on a display screen of the second fluid delivery device, the message notifying the operator of the second fluid delivery device of the presence of the multiple medical devices in the set.

8. The method as in claim 5 further comprising:
receiving a command from the caregiver operating the second fluid delivery device to associate a given medical device in the set to the second fluid delivery device; and
recording an association between the second fluid delivery device and the given medical device.

9. The method as in claim 1,
wherein the association indicates that the third fluid delivery device is assigned for use by the patient; and
wherein the medical information indicates parameters to be used by the second fluid delivery device to deliver a prescribed fluid to the patient.

10. The method as in claim 1 further comprising:
collecting location data indicating where each of multiple patients resides in the medical environment; and
utilizing the location data to associate a respective patient with a corresponding location in the medical environment in which the respective patient resides.

11. The method as in claim 10, wherein the second fluid delivery device indicates a physical location in which the second fluid delivery device resides;
the method further comprising: performing a search in a repository for the medical information associated with the second fluid delivery device, the search including: i) mapping of the physical location to a set of patients that reside in a vicinity of the physical location, and ii) producing the medical information to indicate identities of the patients in the set; and
wherein initiating transmission of the medical information over the network includes initiating display of the identities of the patients in the set on a display screen of the second fluid delivery device.

12. The method as in claim 11 further comprising:
from an operator of the second fluid delivery device, receiving a command to associate the second fluid delivery device to the patient, the patient selected from the set; and
creating an association between the second fluid delivery device and the patient.

13. The method as in claim 12 further comprising:
receiving an inquiry transmitted over the network from the caregiver operating the second fluid delivery device, the inquiry requesting medication order drug information assigned to the patient;
in response to receiving the inquiry, searching the repository for the medication order drug information assigned to the patient; and
transmitting the medication order drug information over the network to the caregiver operating the second fluid delivery device.

14. The method as in claim 13 further comprising:
initiating display of the medication order drug information on a display screen of the second fluid delivery device.

15. The method as in claim 1,
wherein receiving the input over the network includes:
receiving the input from a mobile device operated by the caregiver, the mobile device disparately located with respect to the second fluid delivery device and the third fluid delivery device, the caregiver generating the input to indicate that the third fluid delivery device is assigned to the patient in the medical environment.

16. The method as in claim 1 further comprising:
receiving a first communication from a mobile device operated by the caregiver, the mobile device disparately located with respect to the second fluid delivery device and the third fluid delivery device, the caregiver generating the first communication to indicate that the patient is assigned to the caregiver.

17. The method as in claim 16 further comprising:
receiving a second communication transmitted over the network from the mobile device operated by the caregiver, the second communication requesting a listing of patients assigned to the caregiver;
identifying a set of patients assigned to the caregiver; and
in response to receiving the second communication, transmitting a first reply message over the network to the mobile device operated by the caregiver, the first reply message indicating the set of patients assigned to the caregiver.

18. The method as in claim 17 further comprising:
receiving a third communication transmitted over the network from the mobile device operated by the caregiver, the third communication indicating selection of the patient, the third communication requesting a listing of fluid delivery devices assigned to the patient; and
in response to receiving the third communication, transmitting a second message over the network to the mobile device operated by the caregiver, the second reply message including the listing of fluid delivery devices assigned to the patient.

19. The method as in claim 1, wherein the medical information includes at least one fluid-based drug prescribed for delivery to the patient by the second fluid delivery device.

20. The method as in claim 19 further comprising:
searching a repository and transmitting the medical information over the network to the third fluid delivery device in response to receiving a query from the caregiver of the patient, the query from the caregiver requesting a listing of medicinal fluid prescribed to the patient, the listing including an identity of the first fluid.

21. The method as in claim 20 further comprising:
receiving a communication from the caregiver selecting the first fluid from the listing, the communication indicating that the second fluid delivery device has been selected to deliver the first fluid to the patient; and
recording an association indicating that the first fluid has been assigned for delivery using the second fluid delivery device.

22. The method as in claim 1
wherein the medical information specifies multiple fluid-based drugs prescribed for delivery to the patient, the multiple fluid-based drugs including the first fluid and the second fluid, the method further comprising:
in response to detecting that the first fluid of the multiple fluid-based drugs has been assigned for delivery from the second fluid delivery device, providing notification over the network to the third fluid delivery device assigned for use by the patient, the notification indicating the second fluid of the multiple fluid-based drugs prescribed for delivery to the patient.

23. The method as in claim 22 further comprising:
receiving a communication over the network from the caregiver operating the third fluid delivery device, the communication indicating that the third fluid delivery device has been assigned to deliver the second fluid to the patient; and
in response to receiving the communication, creating an association indicating that the second fluid is being administered to the patient using the third fluid delivery device.

24. The method as in claim 1 further comprising:
prior to receiving the input, initiating a challenge to the caregiver operating the second fluid delivery device to provide appropriate authentication information to operate the second fluid delivery device;
in response to the challenge, receiving a communication over the network from the caregiver, the communication including authentication information to operate the second fluid delivery device;
verifying the authentication information in the communication received from the caregiver; and subsequent to verifying the authentication information provided by the caregiver, transmitting a command over the network to the second fluid delivery device, the command enabling the caregiver to operate the second fluid delivery device and deliver the first fluid to the patient using the second fluid delivery device.

25. A computer system comprising:
a master device
a second fluid delivery device;
a third fluid delivery device;
computer processor hardware; and
a hardware storage resource coupled to the computer processor hardware, the hardware storage resource storing instructions that, when executed by the computer processor hardware, cause the computer processor hardware to perform operations of:
  initiating a group of the master device, second fluid delivery device, and the third fluid delivery device by the master device transmitting a broadcast message with an invitation to the second fluid delivery device and the third fluid delivery device,
  wherein the invitation comprises an identifier for the master device;
  receiving the invitation by the second fluid delivery device and the third fluid delivery device and prompting a user to acknowledge the invitation;
  displaying the invitation by the second fluid delivery device and the third fluid delivery device that the master medical device generated for the second fluid delivery device and the third fluid delivery device to join and initiate formation of the group,
  wherein the identifier for the master device and an identifier for the second fluid delivery device and the third fluid delivery device is stored in a memory,
  receiving input over a network or the group, the input associating the third fluid delivery device to the second fluid delivery device located in a medical environment in which the second fluid delivery device is operated to deliver a first fluid to a patient, the third fluid delivery device operated to deliver a second fluid to the patient;
  recording an association between the second fluid delivery device and the third fluid delivery device as indicated by the received input; and
  initiating transmission of medical information associated with the fluid delivery device over the network to the third fluid delivery device.

26. The computer system as in claim 25, wherein the computer processor hardware further performs operations of:
  associating the medical information with the second fluid delivery device prior to receiving the input over the network to associate the third fluid delivery device to the second fluid delivery device.

27. The computer system as in claim 26, wherein the computer processor hardware further performs operations of:
  receiving the input from the third fluid delivery device, the input generated by a caregiver operating the third fluid delivery device; and
  wherein initiating transmission of the medical information over the network includes communicating the medical information to the third fluid delivery device in response to receiving a search query from the caregiver for the medical information associated with the second fluid delivery device.

28. The computer system as in claim 25, wherein the second fluid delivery device is a fluid pump; and
  wherein the third fluid delivery device is an other fluid pump.

29. The computer system as in claim 25, wherein the computer processor hardware further performs operations of:
  initiating communication with a set of one or more medical devices located in a vicinity of the second fluid delivery device; and
  providing notification to an operator of the second fluid delivery device, the notification indicating the set of one or more medical devices available in a vicinity of the second fluid delivery device for association with the second fluid delivery device.

30. The computer system as in claim 29, wherein providing the notification includes:
  activating a prompt at each respective medical device in the set, the activated prompt indicating that the respective medical device can be programmed to join group including the second fluid delivery device.

31. The computer system as in claim 29, wherein providing the notification includes:
  initiating display of a message on a display screen of the second fluid delivery device, the message notifying the operator of the second fluid delivery device of the presence of the one or more medical devices in the set.

32. The computer system as in claim 29, wherein the computer processor hardware further performs operations of:
  receiving a command from the operator of the second fluid delivery device to associate a given medical device in the set to the second fluid delivery device; and
  recording an association between the second fluid delivery device and the given medical device.

33. The computer system as in claim 25
  wherein the association indicates that the second fluid delivery device is assigned for use by the patient; and
  wherein the medical information indicates parameters to be used by the second fluid delivery device to deliver the prescribed fluid to the patient.

34. The computer system as in claim 25,
  wherein the recorded association indicates that both the third fluid delivery system and the second fluid delivery device are assigned for use by the patient; and
  wherein the medical information indicates the first fluid, the first fluid prescribed fluid for delivery by the second fluid delivery device to the patient.

35. The computer system as in claim 25, wherein the computer processor hardware further performs operations of:
  collecting location data indicating where each of multiple patients resides in the medical environment; and
  utilizing the location data to associate a respective patient with a corresponding location in the medical environment in which the respective patient resides.

36. The computer system as in claim 35, wherein the second fluid delivery device indicates a physical location in which the second fluid delivery device resides;
  wherein searching the repository for medical information associated with the second fluid delivery device includes: i) mapping the location to a set of patients that reside in a vicinity of the location, and ii) producing the medical information to indicate identities of the patients in the set; and
  wherein initiating transmission of the medical information over the network includes initiating display of the identities of the patients in the set on a display screen of the second fluid delivery device.

37. The computer system as in claim 36, wherein the computer processor hardware further performs operations of:
from an operator of the second fluid delivery device, receiving a command to associate the second fluid delivery device to a particular patient selected from the set; and
creating an association between the second fluid delivery device and the particular patient.

38. The computer system as in claim 37, wherein the computer processor hardware further performs operations of:
receiving an inquiry transmitted over the network from an operator of the second fluid delivery device, the inquiry requesting medication order drug information assigned to the particular patient;
in response to receiving the inquiry, searching the repository for the medication order drug information assigned to the particular patient; and
transmitting the medication order drug information over the network to the operator of the second fluid delivery device.

39. The computer system as in claim 38, wherein the computer processor hardware further performs operations of:
initiating display of the medication order drug information on a display screen of the second fluid delivery device.

40. The computer system as in claim 25,
wherein receipt of the input over the network includes: receiving the input from a mobile device operated by a caregiver, the mobile device disparately located with respect to the second fluid delivery device and the third fluid delivery device, the caregiver generating the input to indicate that the third fluid delivery device is being assigned to a particular patient in the medical environment.

41. The computer system as in claim 25, wherein the computer processor hardware further performs operations of:
receiving a first communication from a mobile device operated by a caregiver, the mobile device disparately located with respect to the second fluid delivery device and the third fluid delivery device, the caregiver generating the first communication to indicate that the particular patient in the medical environment is assigned to the caregiver.

42. The computer system as in claim 41, wherein the computer processor hardware further performs operations of:
receiving a second communication transmitted over the network from the mobile device operated by the caregiver, the second communication requesting a listing of patients assigned to the caregiver;
identifying a set of patients assigned to the caregiver; and
in response to receiving the second communication, transmitting a first reply message over the network to the mobile device operated by the caregiver, the first reply message indicating the set of patients assigned to the caregiver.

43. The computer system as in claim 42, wherein the computer processor hardware further performs operations of:
receiving a third communication transmitted over the network from the mobile device operated by the caregiver, the third communication indicating selection of a particular patient in the set, the third communication requesting a listing of second fluid delivery devices assigned to the particular patient; and
in response to receiving the third communication, transmitting a second message over the network to the mobile device operated by the caregiver, the second reply message including the listing of the second fluid delivery devices assigned to the particular patient.

44. The computer system as in claim 25,
wherein the medical information includes an identity of the first fluid, the first fluid prescribed for delivery to the patient by the second fluid delivery device.

45. The computer system as in claim 44, wherein the computer processor hardware further performs operations of:
transmitting the medical information over the network to the second fluid delivery device in response to receiving a query from a caregiver of the patient, the caregiver operating the second fluid delivery device and the third fluid delivery device, the query from the caregiver requesting a listing of medicine prescribed to the patient.

46. The computer system as in claim 45, wherein the computer processor hardware further performs operations of:
producing the listing to include identities of the first fluid and the second fluid;
presenting the listing to the caregiver;
receiving a communication from the caregiver selecting the first fluid in the listing, the communication indicating that the second fluid delivery device has been selected to deliver the first fluid to the patient; and
recording an association indicating that the first fluid has been assigned for delivery using the second fluid delivery device.

47. The computer system as in claim 25,
wherein the second fluid delivery device is assigned for use by the patient;
wherein the medical information specifies multiple fluid-based drugs prescribed for delivery to the patient, the multiple fluid-based drugs including identities of the first fluid and the second fluid, the computer processor hardware further performs operations of:
in response to detecting that the first fluid of the multiple fluid-based drugs has been assigned for delivery from the second fluid delivery device, providing notification over the network to the third fluid delivery device also assigned for use by the patient, the notification indicating the second fluid of the multiple fluid-based drugs prescribed for delivery to the patient.

48. The computer system as in claim 47, wherein the computer processor hardware further performs operations of:
receiving a communication over the network from a caregiver operating the third fluid delivery device, the communication indicating that the third fluid delivery device has been assigned to deliver the second fluid to the patient; and
in response to receiving the communication, creating an association indicating that the second fluid is being administered to the patient using the third fluid delivery device.

49. The computer system as in claim 25, wherein the computer processor hardware further performs operations of:

prior to receiving the input, initiating a challenge to a caregiver operating the second fluid delivery device to provide appropriate authentication information to operate the second fluid delivery device;
in response to the challenge, receiving a communication over the network from the caregiver, the communication including authentication information to operate the second fluid delivery device;
verifying the authentication information in the communication received from the caregiver; and
subsequent to verifying the authentication information provided by the caregiver, transmitting a command over the network to the second fluid delivery device, the command enabling the caregiver to operate the second fluid delivery device and deliver the first fluid to the patient using the second fluid delivery device.

50. Computer-readable hardware storage having instructions stored thereon, the instructions, when carried out by computer processor hardware, causes the computer processor hardware to perform operations of:
initiating a group of the master device, second fluid delivery device, and the third fluid delivery device by the master device transmitting a broadcast message with an invitation to the second fluid delivery device and the third fluid delivery device,
wherein the invitation comprises an identifier for the master device;
receiving the invitation by the second fluid delivery device and the third fluid delivery device and prompting a user to acknowledge the invitation;
displaying the invitation by the second fluid delivery device and the third fluid delivery device that the master medical device generated for the second fluid delivery device and the third fluid delivery device to join and initiate formation of the group,
wherein the identifier for the master device and an identifier for the second fluid delivery device and the third fluid delivery device is stored in a memory,
receiving input over a network or the group, the input associating a third fluid delivery device to a second fluid delivery device located in a medical environment in which the second fluid delivery device is operated to deliver a first fluid to a patient, the third fluid delivery device operated to deliver a second fluid to the patient;
recording an association between the second fluid delivery device and the third fluid delivery device as indicated by the received input; and
initiating transmission of medical information associated with the second fluid delivery device over the network to the third fluid delivery device.

51. The method as in claim 1 further comprising:
activating a prompt at each respective medical device in a set, the activated prompt indicating that the respective medical device can be programmed to join a group including the second fluid delivery device assigned to the patient.

52. The method as in claim 1, wherein the association is an assignment, the assignment indicating that the second fluid delivery device and the third fluid delivery device are both assigned for use by the patient; and
wherein the medical information indicates parameters assigned for use by the second fluid delivery device to deliver the first fluid to the patient.

53. The method as in claim 52, wherein, via the association, the third fluid delivery device is operable to detect that the first fluid is already being delivered by the second fluid delivery device to the particular patient.

54. The method as in claim 1, wherein, via the association, the third fluid delivery device is operable to detect that the first fluid being delivered by the second fluid delivery device to the patient is incompatible with the second fluid assigned for delivery by the third fluid delivery device to the patient.

55. The method as in claim 54, wherein the third fluid delivery device generates a warning in response to being informed of the incompatibility between the first fluid and the second fluid.

56. The method as in claim 1 further comprising:
based on a total fluid volume infused into the patient by the second fluid delivery device and the third fluid delivery device, generating a warning.

57. The method as in claim 1 further comprising:
conveying fluid delivery setting information associated with the second fluid delivery device to the third fluid delivery device.

58. The method as in claim 1 further comprising:
maintaining a list of medication orders including first orders that have been delivered to the patient and second orders that are being delivered to the patient.

59. The method as in claim 1 further comprising:
controlling delivery of prescribed fluid that has not yet been delivered to the patient.

60. The method as in claim 1, wherein the association indicates that the second fluid delivery device and the third fluid delivery device are being monitored by the caregiver; and
wherein the medical information indicates parameters to be used to deliver the second fluid to the patient being cared for by the caregiver.

61. The method as in claim 60 further comprising:
providing an alert to the caregiver, the alert indicating the second fluid delivered by the third fluid delivery device to the patient.

62. The method as in claim 1 further comprising:
identifying a patient-care provider association based on: i) a first association, the first association indicating a respective association of the second fluid delivery device to the patient, and ii) a second association, the second association indicating a respective association between the caregiver and the second fluid delivery device.

63. The method as in claim 1 further comprising:
in response to receiving a query, based on patient and care provider associations, displaying patient information associated with the patient to the caregiver.

64. The method as in claim 1 further comprising:
assigning the second fluid delivery device and the third fluid delivery device to the patent;
assigning the second fluid delivery device and the third fluid delivery device to the caregiver caring for the patient;
assigning the patient to a location in which the second fluid delivery device and the third fluid delivery device are used to deliver prescribed fluid, the prescribed fluid including the first fluid and second fluid.

65. The method as in claim 1 further comprising:
conveying a notification to the third fluid delivery device, the notification indicating that the second fluid delivery device is operated to deliver the first fluid to the patient.

66. The method as in claim 1, wherein the second fluid delivery device is assigned for use by the patient in the medical environment; and
wherein the input indicates that the caregiver assigns the third fluid delivery device for use by the patient, the association indicating that the third fluid delivery device is used in conjunction with the second fluid delivery device to deliver fluid to the patient.

67. The method as in claim 1, wherein the displayed medical information indicates a drug in the first fluid delivered to the recipient via the second fluid delivery device.

68. The method as in claim 67 further comprising:
controlling operation of the third fluid delivery device to deliver the second fluid to the patient based at least in part on the drug indicated by the medical information.

69. The method as in claim 1, wherein initiating display of the medical information includes:
initiating display of an identity of the second fluid on the display screen, the second fluid prescribed for delivery to the patient in addition to the first fluid.

70. The method as in claim 69, wherein receiving the fluid delivery selection includes:
detecting that the caregiver selects the identity of the second fluid displayed on the display screen of the third fluid delivery device, selection of the identity of the second fluid being the fluid delivery selection by the caregiver.

71. The method as in claim 1, wherein the master device is automatically part of the group because it sent the invitation to the second fluid delivery device and the third fluid delivery device.

72. The method as in claim 1, wherein a visual prompt displayed by the second fluid delivery device and the third fluid delivery device after receiving the invitation from the master device indicates patient and location information associated with a patient for which the group was created.

* * * * *